United States Patent
Brotherton-Pleiss et al.

(10) Patent No.: US 6,627,644 B2
(45) Date of Patent: Sep. 30, 2003

(54) 4-PIPERIDINYL ALKYL AMINE DERIVATIVES AS MUSCARINIC RECEPTOR ANTAGONISTS

(75) Inventors: Christine E. Brotherton-Pleiss, Sunnyvale, CA (US); Ann Marie Madera, Dublin, CA (US); Robert James Weikert, Boulder Creek, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/308,081

(22) Filed: Dec. 2, 2002

(65) Prior Publication Data

US 2003/0162780 A1 Aug. 28, 2003

Related U.S. Application Data

(60) Provisional application No. 60/336,795, filed on Dec. 3, 2001.

(51) Int. Cl.$^7$ ............... A61K 31/445; C07D 211/06
(52) U.S. Cl. ............ 514/319; 546/195; 546/189; 546/188; 544/129; 544/360; 514/316; 514/252; 514/235.5
(58) Field of Search ............... 514/319, 316, 514/235.5, 252; 546/195, 189, 188; 544/129, 360

(56) References Cited

U.S. PATENT DOCUMENTS 5,179,108 A  1/1993  George et al.

6,319,920 B1  11/2001  Caroon et al.
2002/0004494 A1  1/2002  Weikert et al.
2002/0004501 A1  1/2002  Dvorak et al.

FOREIGN PATENT DOCUMENTS

| EP | 0447292 A1 | 9/1991 |
| EP | 0 270 947 B1 | 5/1993 |
| FR | 2 659 853 A1 | 9/1991 |
| WO | WO 89/09050 A1 | 10/1989 |

*Primary Examiner*—Charanjit S. Aulakh
(74) *Attorney, Agent, or Firm*—Brian Buckwalter Rohan Peries

(57) ABSTRACT

This invention relates to compounds which are generally muscarinic receptor antagonists and which are represented by Formula I:

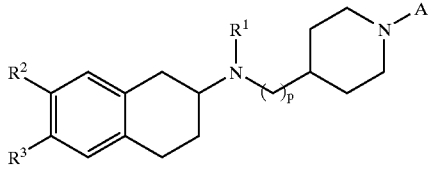

wherein p, $R^1$, $R^2$, $R^3$ and A are as defined in the specification, or individual isomers, racemic or non-racemic mixtures of isomers, or acceptable salts or solvates thereof. The invention further relates to pharmaceutical compositions containing such compounds and methods for their use and preparation as therapeutic drugs.

41 Claims, No Drawings

4-PIPERIDINYL ALKYL AMINE DERIVATIVES AS MUSCARINIC RECEPTOR ANTAGONISTS

CROSS-REFERENCE

This application claims the benefit of priority of U.S. Provisional Patent Application Serial No. 60/336,795, filed Dec. 3, 2001, which is incorporated herein by reference in its entirety.

FIELD OF THE INVENTION

This invention relates to benzocycloalkylenylamine derivatives, associated pharmaceutically acceptable salts, or hydrates thereof, and associated pharmaceutical compositions and methods for use as selective muscarinic receptor antagonists.

BACKGROUND OF THE INVENTION

Acetylcholine (Ach) is the principal transmitter of the parasympathetic nervous system. The physiological actions of Ach are mediated by activation of either nicotinic or muscarinic receptors. Both of these receptor classes are heterogeneous: e.g., the muscarinic receptor family comprises five subtypes ($M_1$, $M_2$, $M_3$, $M_4$, and $M_5$) each encoded by distinct genes and possessing unique pharmacology and distribution.

Almost all smooth muscle tissues express both muscarinic M2 and M3 receptors, both of which have a functional role. M2 receptors outnumber M3 receptors by a proportion of approximately 4 to 1. Generally, M3 receptors mediate the direct contractile effects of acetylcholine in the vast majority of smooth muscle tissues. M2 receptors, on the other hand, cause smooth muscle contraction indirectly by inhibiting sympathetically (β-adrenoreceptor)-mediated relaxation.

Compounds that act as antagonists of muscarinic receptors have been used to treat several disease states associated with improper smooth muscle function, as well as in the treatment of cognitive and neurodegenerative disorders such as Alzheimer's disease. Until recently, most of these compounds have been non-selective for the various muscarinic receptor subtypes, leading to unpleasant anti-cholinergic side-effects such as dry mouth, constipation, blurred vision, or tachycardia. The most common of these side-effects is dry-mouth resulting from muscarinic receptor blockade in the salivary gland. Recently developed M2 and/or M3 specific antagonists have been shown to have reduced side effects. Evidence suggests that blockade of M2 and/or M3 receptors over M5 receptor could be therapeutically effective in the treatment of disease states associated with smooth muscle disorders.

Additionally, muscarinic receptor antagonists are front-line therapy as bronchodilators in chronic obstructive pulmonary disease (COPD). It is thought that the efficacy of this class of molecules is mediated through antagonism of the natural transmitter (acetylcholine) at M3 receptors on airway smooth muscle and there may be additional benefit in COPD through inhibition of mucus secretion which may also be mediated through M3 receptors. The current standard anti-muscarinic for the treatment of COPD is ipratropium (Atrovent) which is administered by aerosol 4 times per day. More recently tiotropium (Spiriva) has been developed by Boehringer-Ingelheim as a second-generation muscarinic antagonist and is expected to be launched in 2002 (in collaboration with Pfizer). Tiotropium is also given by aerosol but has a slow off-rate from the M3 receptor and, as a result, causes a prolonged bronchodilatation. Tiotropium will be given once per day. Although tiotropium has high affinity for all muscarinic receptor subtypes, it is a quaternary ammonium compound which is poorly absorbed.

Few M2 and/or M3 selective antagonists have been developed. The present invention fills this need by providing these types of antagonists useful in the treatment of disease states associated with improper smooth muscle function and respiratory disorders.

SUMMARY OF THE INVENTION

This invention relates to compounds comprising Formula I:

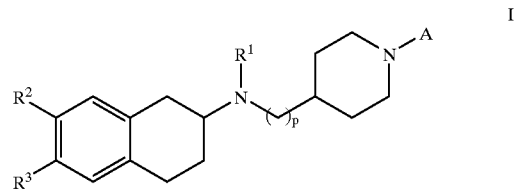

wherein:

A is —C(O)R$^4$ or —S(O)$_2$R$^5$;

R$^1$ is (C$_{1-6}$)alkyl or allyl;

R$^2$ and R$^3$ are independently in each occurrence hydrogen, halogen, (C$_{1-6}$)alkyl, haloalkyl, —OR', —S(O)$_{0-2}$R', —NR'R", —NR'COR", —NR'"CONR'R", —NR'SO$_2$R", —NR'"SO$_2$NR'R", —SO$_2$NR'R", —OSO$_2$R', nitro, cyano, heteroaryl, or aryl, wherein said heteroaryl or aryl group is optionally substituted with one or more groups selected from hydroxy, cyano, (C$_{1-6}$)alkyl, (C$_{1-6}$)alkoxy, haloalkoxy, alkylthio, halo, haloalkyl, hydroxyalkyl, nitro, alkoxycarbonyl, amino, alkylamino, alkylsulfonyl, alkylcarbonyl, alkylaminosulfonyl, alkylsulfonylamino, alkylaminocarbonyl, and alkylcarbonylamino, with the proviso that R$^2$ and R$^3$ are not both hydrogen;

R', R", and R'" are independently in each occurrence hydrogen, (C$_{1-6}$)alkyl, (C$_3$–C$_6$)cycloalkyl, haloalkyl, diphenylmethyl, aryl or aryl(C$_{1-6}$)alkyl, wherein the aryl group is optionally substituted with one or more groups selected from hydroxy, cyano, (C$_{1-6}$)alkyl, (C$_{1-6}$)alkoxy, haloalkoxy, alkylthio, halo, haloalkyl, hydroxyalkyl, nitro, alkoxycarbonyl, amino, alkylamino, alkylsulfonyl, alkylcarbonyl, alkylaminosulfonyl, alkylsulfonylamino, alkylaminocarbonyl, alkylcarbonylamino and phenyl;

heterocycyl, wherein the heterocylcyl group is optionally substituted with one or more groups selected from hydroxy, oxo, cyano, (C$_{1-6}$)alkyl, (C$_{1-6}$)alkoxy, haloalkoxy, alkylthio, halo, and haloalkyl;

heteroaryl, wherein the heteroaryl is optionally substituted with one or more groups selected from (C$_{1-6}$) alkyl, (C$_{1-6}$)alkoxy, and halogen;

or R' and R" together with the nitrogen they are attached may also form a 5- to 7-membered ring, optionally incorporating one additional heteroatom chosen from O, N, or S(O)$_{0-2}$, said ring being optionally substituted with one or two (C$_{1-6}$)alkyl groups;

R$^4$ is (C$_{1-6}$)alkyl, haloalkyl, benzyloxy, diphenylmethyl, —NR$^a$R$^b$, wherein R$^a$ and R$^b$ are as defined herein, —Y-heterocyclyl, —Y-heteroaryl, wherein the heterocyclyl and heteroaryl groups are independently of each other optionally substituted with one or more groups selected from $(C_{1-6})$alkyl, $(C_{1-6})$alkoxy, halo, haloalkyl, alkylsulfonyl, alkylaminosulfonyl, and alkylsulfonylamino, and wherein Y is a bond or $(C_{1-3})$ alkylene;

$R^a$ is hydrogen, $(C_{1-6})$alkyl, haloalkyl, cycloalkyl or aryl, wherein the cycloalkyl or the aryl group are each independently of each other optionally substituted with $(C_{1-6})$alkyl, $(C_{1-6})$alkoxy, halo, haloalkyl, and alkylsulfonyl;

$R^b$ is hydrogen or $(C_{1-6})$alkyl;

or $R^a$ and $R^b$ together with the nitrogen they are attached may also form a 5- to 7-membered ring, optionally incorporating one additional heteroatom chosen from O, N, or $S(O)_{0-2}$, said ring being optionally substituted with one or two $(C_{1-6})$alkyl groups;

$R^5$ is $(C_{1-6})$alkyl, haloalkyl, —$NR^aR^b$, wherein $R^a$ and $R^b$ are as defined above, aryl or heteroaryl, wherein the aryl or heteroaryl are each independently of each other optionally substituted with one or two groups selected from $(C_{1-6})$alkyl, $(C_{1-6})$alkoxy, halo, and alkylsulfonyl; and p is an integer from 1 to 2 inclusive;

or prodrugs, individual isomers, racemic or non-racemic mixtures of isomers, and pharmaceutically acceptable salts or solvates thereof.

In another aspect, the invention relates to pharmaceutical compositions containing a therapeutically effective amount of at least one compound of Formula I, or individual isomers, racemic or non-racemic mixtures of isomers and salts or solvates thereof, in admixture with at least one suitable carrier.

In another aspect, this invention relates to a method of treatment of a disease in a mammal treatable by administration of at least one compound of Formula I, having selective activity for the muscarinic receptors, in particular a method of treatment in a subject having a disease state comprising smooth muscle disorders, preferably genitourinary tract disorders, respiratory tract disorders, gastrointestinal tract disorders; more preferably genitourinary tract disorders such as overactive bladder or detrusor hyperactivity and its symptoms, such as the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity and the like; and the symptoms usually manifested in detrusor hyperreflexia (neurogenic bladder), in conditions such as outlet obstruction, outlet insufficiency, pelvic hypersensitivity, or in idiopathic conditions such as detrusor instability, and the like. In another preferred embodiment, the disease comprises respiratory tract disorders such as allergies and asthma. In another preferred embodiment, the disease state comprises gastrointestinal disorders. In another preferred embodiment, the disease state comprises cognitive and neurodegenerative disorders.

In another aspect, the invention relates to a process for preparing a compound of Formula I, which process comprises reacting a compound of formula d:

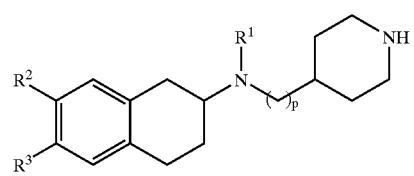

wherein p, $R^1$, $R^2$, and $R^3$ are as described in the summary of the invention, with a compound of formula $R^4C(O)L$ or $R^5 S(O)_2L$, wherein L is a leaving group, and $R^4$ and $R^5$ are as described in the summary of the invention, to give a compound of Formula I:

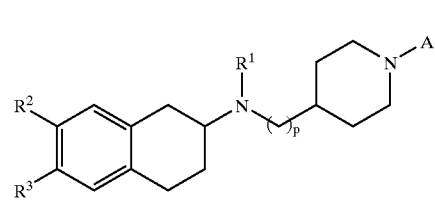

wherein $R^1$, $R^2$, $R^3$, p and A are as described in the summary of the invention.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an", and "the" include plural referents unless the context clearly dictates otherwise.

"Alkyl" or "lower alkyl" means the monovalent linear or branched saturated hydrocarbon radical, having from one to six carbon atoms inclusive, unless otherwise indicated. Examples of lower alkyl radicals include, but are not limited to, methyl, ethyl, propyl, isopropyl, 1-ethylpropyl, sec-butyl, tert-butyl, n-butyl, n-pentyl, n-hexyl, and the "Substituted lower alkyl" means the lower alkyl as defined herein, including one to three substituents, preferably one substituent such as hydroxyl, alkoxy, amino, amido, carboxyl, acyl, halogen, cyano, nitro, or thiol. These groups may be attached to any carbon atom of the lower alkyl moiety. Examples of substituted lower alkyl radicals include, but are not limited to, 2-methoxyethyl, 2-hydroxyethyl, dimethyl-aminocarbonylmethyl, 4-hydroxy-2,2-dimethyl-butyl, trifluoromethyl, trifluorobutyl and the like.

"Alkoxy" means the radical —O—R, wherein R is a lower alkyl radical as defined herein. Examples of alkoxy radicals include, but are not limited to, methoxy, ethoxy, isopropoxy, and the like.

"Aryl" means the monovalent aromatic carbocyclic radical consisting of one individual ring, or one or more fused rings in which at least one ring is aromatic in nature, which can optionally be substituted with one or more, preferably one or two, substituents selected from hydroxy, cyano, lower alkyl, lower alkoxy, haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, biphenyl, indanyl, anthraquinolyl, tert-butyl-phenyl, 1,3-benzodioxolyl, and the like.

"Arylalkyl" means the radical R'R"—, wherein R' is an aryl radical as defined herein, and R" is an alkyl radical as defined herein. Examples of arylalkyl radicals include, but are not limited to, benzyl, phenylethyl, 3-phenylpropyl, and the like.

"Cycloalkyl" means the monovalent saturated carbocyclic radical consisting of one or more rings, preferably one or two rings, of three to ten carbons per ring, which can optionally be substituted with one or more, preferably one or two substitutents, selected from hydroxy, cyano, lower alkyl, lower alkoxy, haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonyl-amino, and arylcarbonylamino, unless otherwise indicated. Examples of cycloalkyl radicals include, but are not limited to, cyclopropyl, cyclobutyl, 3-ethylcyclobutyl, cyclopentyl, cycloheptyl, adamantanyl and the like.

"Heteroaryl" means the monovalent aromatic cyclic radical having one or more rings, preferably one to three rings, of four to eight atoms per ring, incorporating one or more heteroatoms, preferably one or two, within the ring (chosen from nitrogen, oxygen, or sulfur), which can optionally be substituted with one or more, preferably one or two substituents selected from hydroxy, cyano, lower alkyl, lower alkoxy, haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino, unless otherwise indicated. Examples of heteroaryl radicals include, but are not limited to, imidazolyl, oxazolyl, thiazolyl, pyrazinyl, thienyl, furanyl, pyridinyl, quinolinyl, isoquinolinyl, benzofuryl, benzothiophenyl, benzothiopyranyl, benzimidazolyl, benzoxazolyl, benzothiazolyl, benzopyranyl, indazolyl, indolyl, isoindolyl, quinolinyl, isoquinolinyl, naphthyridinyl, benezenesulfonyl-thiophenyl, and the like.

"Heterocyclyl" means the monovalent saturated cyclic radical, consisting of one or more rings, preferably one to two rings, of three to eight atoms per ring, incorporating one or more ring heteroatoms (chosen from N, O or $S(O)_{0-2}$), and which can optionally be substituted with one or more, preferably one or two substituents selected from hydroxy, oxo, cyano, lower alkyl, lower alkoxy, haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonyl-amino, and arylcarbonylamino, unless otherwise indicated. Examples of heterocyclic radicals include, but are not limited to, morpholinyl, piperazinyl, piperidinyl, pyrrolidinyl, tetrahydropyranyl, thiomorpholinyl, and the like.

"Halogen" means the radical fluoro, bromo, chloro, and/or iodo.

"Haloalkyl" means the lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Haloalkoxy" means the radical —OR, wherein R is a haloalkyl as defined above.

"Hydroxyalkyl" means the lower alkyl radical as defined herein, substituted with one or more hydroxy groups. Examples of hydroxyalkyl radicals include, but are not limited to, hydroxymethyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, 2-(hydroxymethyl)-3-hydroxypropyl, and the like.

"Alkoxycarbonyl" or "alkyl ester" means the radical —C(O)—O—R, wherein R is a lower alkyl radical as defined herein. Examples of alkoxycarbonyl radicals include, but are not limited to, methoxycarbonyl, ethoxycarbonyl, sec-butoxycarbonyl, isopropyloxycarbonyl, and the like.

"Aryloxycarbonyl" or "aryl ester" means the radical —C(O)—O—R, wherein R is an aryl radical as defined herein. Examples of aryloxycarbonyl radicals include, but are not limited to phenyl ester, naphthyl ester, and the like.

"Alkylcarbonyl" (or "acyl") means the radical —C(O)—R, wherein R is a lower alkyl radical as defined herein. Examples of alkylcarbonyl radicals include, but are not limited to, acetyl, propionyl, n-butyryl, sec-butyryl, t-butyryl, iso-propionyl and the like.

"Alkylaminocarbonyl" means the radical —C(O)NR'R", wherein R' is lower alkyl as defined herein, and R" is hydrogen or lower alkyl as defined herein. Examples of alkylaminocarbonyl include, but are not limited to methylaminocarbonyl, dimethylaminocarbonyl, t-butylaminocarbonyl, n-butylaminocarbonyl, iso-propylaminocarbonyl, and the like.

"Alkylcarbonylamino" means the radical —NC(O)R', wherein R' is lower alkyl as defined herein. Examples of alkylcarbonylamino include, but are not limited to methylcarbonylamino, iso-propylcarbonylamino, t-butylcarbonylamino, and the like.

"Alkylaminosulfonyl" means the radical —S(O)$_2$NR'R", wherein R' is lower alkyl as defined herein, and R" is hydrogen or lower alkyl as defined herein. Examples of alkylaminosulfonyl include, but are not limited to methylaminosulfonyl, dimethylaminosulfonyl, and the like.

"Alkylsulfonylamino" means the radical —NS(O)$_2$R', wherein R' is lower alkyl as defined herein. Examples of alkylsulfonylamino include, but are not limited to methylsulfonylamino, propylsulfonylamino, and the like.

"Alkylsulfonyl" means the radical —S(O)$_2$R, wherein R is lower alkyl or a substituted lower alkyl as defined herein. Examples of alkylsulfonyl include, but are not limited to methylsulfonyl, trifluoromethylsulfonyl, propylsulfonyl, and the like.

"Alkylsulfonyloxy" means the radical —OS(O)$_2$R, wherein R is lower alkyl or substituted lower alkyl as defined herein. Examples of alkylsulfonyloxy include, but are not limited to methylsulfonyloxy, trifluoromethyl-sulfonyloxy, propylsulfonyloxy, and the like.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Leaving group" means the group with the meaning conventionally associated with it in synthetic organic chemistry, i.e., an atom or group displaceable under alkylating conditions. Examples of leaving groups include, but are not limited to, halogen, alkane- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively includes groups protected as acetates, haloalkyl carbonates, benzyl ethers, alkylsilyl ethers, heterocyclyl ethers, and methyl or alkyl ethers, and the like. Protective or blocking groups for carboxyl groups are similar to those described for hydroxyl groups, preferably tert-butyl, benzyl or methyl esters. Examples of protecting groups can be found in T. W. Greene et al., *Protective Groups in Organic Chemistry*, (J. Wiley, $2^{nd}$ ed. 1991) and Harrison et al., *Compendium of Synthetic Organic Methods*, Vols. 1–8 (J. Wiley and Sons 1971–1996).

"Amino-protecting group" means the protecting group that refers to those organic groups intended to protect the nitrogen atom against undesirable reactions during synthetic procedures and includes, but is not limited to, benzyl, benzyloxycarbonyl (carbobenzyloxy, Cbz), p-methoxybenzyloxycarbonyl, p-nitrobenzyloxycarbonyl, tert-butoxycarbonyl (Boc), trifluoroacetyl, and the like. It is preferred to use either Boc or Cbz as the amino-protecting group because of the relative ease of removal, for example by acids in the case of Boc, e.g., trifluoroacetic acid or hydrochloric acid in ethyl acetate; or by catalytic hydrogenation in the case of Cbz.

"Deprotection" or "deprotecting" means the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxide in alcoholic solutions, zinc in methanol, acetic acid, trifluoroacetic acid, palladium catalysts, or boron tribromide, and the like.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al. (1966) *Angew. Chem. Inter.* Edit., 5, 385; errata 511; Cahn et al. (1966) *Angew. Chem.*, 78, 413; Cahn and Ingold (1951) *J. Chem. Soc.* (London), 612; Cahn et al. (1956) *Experientia*, 12, 81; Cahn, J. (1964) *Chem.Educ.*, 41,116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

"Substantially pure" means at least about 80 mole percent, more preferably at least about 90 mole percent, and most preferably at least about 95 mole percent of the desired enantiomer or stereoisomer is present.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from hydrochloric acid, trifluoroacetic acid, dibenzoyl-L-tartaric acid, and phosphoric acid.

It should be understood that all references to pharmaceutically acceptable salts include solvent addition forms (solvates) or crystal forms (polymorphs) as defined herein, of the same acid addition salt.

"Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" means a pharmacologically inactive form of a compound which must be metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in *The Organic Chemistry of Drug Design and Drug Action*, by Richard B. Silverman, Academic Press, San Diego, 1992. Chapter 8: "Prodrugs and Drug delivery Systems" pp.352–401; *Design of Prodrugs*, edited by H. Bundgaard, Elsevier Science, Amsterdam, 1985; *Design of Biopharmaceutical Properties through Prodrugs and Analogs*, Ed. by E. B. Roche, American Pharmaceutical Association, Washington, 1977; and *Drug Delivery Systems*, ed. by R. L. Juliano, Oxford Univ. Press, Oxford, 1980.

"Subject" means mammals and non-mammals. Mammals means any member of the Mammalia class including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like.

"Therapeutically effective amount" means an amount of a compound that, when administered to a subject for treating a disease state, is sufficient to effect such treatment for the disease state. The "therapeutically effective amount" will vary depending on the compound and disease state being treated, the severity of the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. In one preferred embodiment, a pharmacological effect means that primary indications of the subject being treated are prevented, alleviated, or reduced. For example, a pharmacological effect would be one that results in the prevention, alleviation or reduction of primary indications in a treated subject. In another preferred embodiment, a pharmacological effect means that disorders or symptoms of the primary indications of the subject being treated are prevented, alleviated, or reduced. For example, a pharmacological effect would be one that results in the prevention or reduction of primary indications in a treated subject.

"Disease state" means any disease, condition, symptom, or indication.

"Treating" or "treatment" of a disease state includes:

(1) preventing the disease state, i.e. causing the clinical symptoms of the disease state not to develop in a subject that may be exposed to or predisposed to the disease state, but does not yet experience or display symptoms of the disease state;

(2) inhibiting the disease state, i.e., arresting the development of the disease state or its clinical symptoms; or (3) relieving the disease state, i.e., causing temporary or permanent regression of the disease state or its clinical symptoms.

"Antagonist" means a molecule such as a compound, a drug, an enzyme inhibitor, or a hormone, that diminishes or prevents the action of another molecule or receptor site.

"Disorders of the urinary tract" or "uropathy" used interchangeably with "symptoms of the urinary tract" means the pathologic changes in the urinary tract. Symptoms of the urinary tract include overactive bladder (also known as detrusor hyperactivity), outlet obstruction, outlet insufficiency, and pelvic hypersensitivity.

"Overactive bladder" or "Detrusor hyperactivity" includes, but is not limited to, the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

"Outlet obstruction" includes, but is not limited to, benign prostatic hypertrophy (BPH), urethral stricture disease, tumors and the like. It is usually symptomatically manifested as obstructive (low flow rates, difficulty in initiating urination, and the like), or irritative (urgency, suprapubic pain, and the like).

"Outlet insufficiency" includes, but is not limited to, urethral hypermobility, intrinsic sphincteric deficiency, or mixed incontinence. It is usually symptomatically manifested as stress incontinence.

"Pelvic Hypersensitivity" includes but is not limited to, pelvic pain, interstitial (cell) cystitis, prostadynia, prostatis, vulvadynia, urethritis, orchidalgia, and the like. It is symptomatically manifested as pain, inflammation or discomfort referred to the pelvic region, and usually includes symptoms of overactive bladder.

Throughout the application the following abbreviations are used with the following meanings:

| | |
|---|---|
| Bnz | benzyl |
| Boc (or boc) | ter-butoxycarbonyl |
| BPH | Benign prostatic hypertrophy or benign prostatic hyperplasia |
| DIEA | Diisopropylethylamine |
| DMF | N,N-Dimethylformamide |
| DMSO | Dimethylsulfoxide |
| EDCI | 1-(3-Dimethylaminopropyl)-3-ethylcarbodiimide hydrochloride |

| | |
|---|---|
| EtOAc | Ethyl acetate |
| Hal | Halogen or halide |
| HOBT | 1-Hydroxybenzotriazole hydrate |
| Pro | Protective group |
| RPHPLC | Reverse phase high pressure liquid chromatography |
| TFA | Trifluoroacetic acid |
| TFAA | Trifluoroacetic acid anhydride |
| THF | Tetrahydrofuran |

Nomenclature

The naming and numbering of the compounds of this invention is illustrated below:

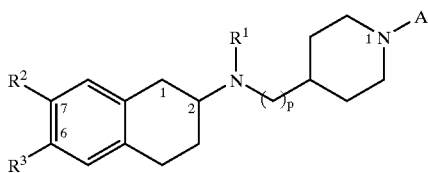

In general, the nomenclature used in this Application is based on AUTONOM™ v.4, a Beilstein Institute computerized system for the generation of IUPAC systematic nomenclature.

A compound of Formula I wherein $R^2$ and $R^3$ are methoxy, R' is propyl, p is 1, A is —C(O)$R^4$ and $R^4$ is —N(CH$_3$)$_2$ is named 4-{[(6,7-Dimethoxy-1,2,3,4-tetrahydro-naphthalen-2-yl)-propyl-amino]-methyl}-piperidine-1-carboxylic acid dimethylamide.

Preferred Compounds

Among compounds of the present invention set forth in the Summary of the Invention, certain compounds of Formula I, or prodrugs, individual isomers, racemic or non-racemic mixtures of isomers, or pharmaceutically acceptable salts or solvates thereof, are preferred:

In a preferred embodiment $R^2$ and $R^3$ are —OR', —NO$_2$, —OSO$_2$R', aryl, or hydrogen, with the proviso that $R^2$ and $R^3$ are not both hydrogen; more preferably $R^2$ and $R^3$ are hydrogen or —OR', wherein R' is (C$_{1-6}$)alkyl or haloalkyl, with the proviso that $R^2$ and $R^3$ are not both hydrogen.

In another preferred embodiment A is —C(O)$R^4$. Within this preferred embodiment a preferred group of compounds is that wherein $R^1$ is (C$_{1-6}$)alkyl. Within the foregoing embodiment another preferred group of compounds is that wherein $R^4$ is —NR$^a$R$^b$, preferably that wherein $R^4$ is —NR$^a$R$^b$ and R$^a$ is (C$_{1-6}$)alkyl or aryl, and R$^b$ is hydrogen or (C$_{1-6}$)alkyl, or R$^a$ and R$^b$ together with the nitrogen they are attached may also form a 5- to 7-membered ring, optionally incorporating one additional heteroatom chosen from O, N, or S(O)$_{0-2}$, said ring being optionally substituted with one or two (C$_{1-6}$)alkyl groups. Another preferred group of compounds is that wherein $R^4$ is —NR$^a$R$^b$ and R$^a$ and R$^b$ together with the nitrogen they are attached form a piperidine ring, said piperidine ring being optionally substituted with one or two (C$_{1-6}$)alkyl groups. Another preferred group of compounds is that wherein $R^4$ is —NR$^a$R$^b$ and R$^a$ and R$^b$ together with the nitrogen they are attached form pyrrolidine ring, said pyrrolidine ring being optionally substituted with one or two (C$_{1-6}$)alkyl groups. Another preferred group of compounds is that wherein $R^4$ is —NR$^a$R$^b$ and R$^a$ and R$^b$ together with the nitrogen they are attached form a piperazine ring, said piperazine ring being optionally substituted with one or two (C$_{1-6}$) alkyl groups. Another preferred group of compounds is that wherein $R^4$ is —NR$^a$R$^b$ and R$^a$ and R$^b$ together with the nitrogen they are attached form a morpholine ring, said morpholine ring being optionally substituted with one or two (C$_{1-6}$)alkyl groups. Within the embodiment wherein $R^4$ is —NR$^a$R$^b$, another group of compounds is that wherein $R^2$ and $R^3$ are hydrogen or —OR', wherein R' is (C$_{1-6}$)alkyl or haloalkyl, with the proviso that $R^2$ and $R^3$ are not both hydrogen, and in another subgroup within this embodiment $R^1$ is ethyl or propyl.

In another preferred embodiment A is —C(O)$R^4$ and $R^4$ is (C$_{1-6}$)alkyl or haloalkyl. Within this embodiment $R^2$ and $R^3$ are hydrogen or —OR', wherein R' is (C$_{1-6}$)alkyl or haloalkyl, with the proviso that $R^2$ and $R^3$ are not both hydrogen, and in another subgroup within this embodiment $R^1$ is ethyl or propyl.

In another preferred embodiment A is —C(O)$R^4$ and $R^4$ is —Y-heterocyclyl, or —Y-heteroaryl, and —Y— is a bond or a (C$_{1-3}$) alkylene. Within this embodiment a preferred group of compounds is that wherein the heteroaryl group is selected from the group of furan, thiophene, isoxazole, oxazole, or imidazole, and in another embodiment the preferred group of compounds is that wherein the heterocyclyl is a piperidine group optionally substituted with one or more (C$_{1-6}$)alkyl groups. Within this embodiment $R^2$ and $R^3$ are hydrogen or —OR', wherein R' is (C$_{1-6}$)alkyl or haloalkyl, with the proviso that $R^2$ and $R^3$ are not both hydrogen, and in another subgroup within this embodiment $R^1$ is ethyl or propyl.

In another preferred embodiment A is —S(O)$_2$R$^5$, and within this embodiment a preferred group of compounds is that wherein $R^5$ is (C$_{1-6}$)alkyl or haloalkyl. Another preferred group of compounds is that wherein $R^5$ is —NR$^a$R$^b$, and even more preferred that wherein $R^5$ is —NR$^a$R$^b$ and R$^a$ is (C$_{1-6}$)alkyl or aryl, and R$^b$ is hydrogen or (C$_{1-6}$)alkyl, or R$^a$ and R$^b$ together with the nitrogen they are attached may also form a 5- to 7-membered ring, optionally incorporating one additional heteroatom chosen from O, N, or S(O)$_{0-2}$, said ring being optionally substituted with one or two (C$_{1-6}$)alkyl groups.

Another preferred embodiment is that wherein A is —S(O)$_2$R$^5$ and $R^5$ is aryl, more preferably that wherein $R^5$ is phenyl, optionally substituted with one or more groups selected from (C$_{1-6}$)alkyl, (C$_{1-6}$)alkoxy, halo, and alkylsulfonyl.

Another preferred embodiment is that wherein A is —S(O)$_2$R$^5$ and $R^5$ is heteroaryl, and in even more preferred is that wherein the heteroaryl is selected from the group of furan, thiophene, oxazole and imidazole, all optionally substituted with one or two groups selected from (C$_{1-6}$)alkyl groups, (C$_{1-6}$)alkoxy, halo, and alkylsulfonyl.

Exemplary preferred compounds, or individual isomers, racemic or non-racemic mixtures of isomers, or pharmaceutically acceptable salts or solvates thereof comprise:

(7-Bromo-1,2,3,4-tetrahydro-naphthalen-2-yl)-(1-methanesulfonyl-piperidin-4ylmethyl)-propyl-amine;

(4-{[(7-Methoxy-1,2,3,4-tetrahydro-naphthalen-2-yl)-propyl-amino]-methyl}-piperidin-1-yl)-piperidin-4-yl-methanone;

(1-Methanesulfonyl-piperidin-4-ylmethyl)-(7-methoxy-1,2,3,4-tetrahydro-naphthalen-2-yl)-propyl-amine;

4-{[(6,7-Dimethoxy-1,2,3,4-tetrahydro-naphthalen-2-yl)-propyl-amino]-methyl}-piperidine-1-carboxylic acid dimethylamide;

(4-{[(7-Methoxy-1,2,3,4-tetrahydro-naphthalen-2-yl)-propyl-amino]-methyl}-piperidin-1-yl)-morpholin-4-yl-methanone;

(1-Methanesulfonyl-piperidin-4-ylmethyl)-(7-methoxy-1,2,3,4-tetrahydro-naphthalen-2-yl)-propyl-amine; and (4-{([(6,7-Dimethoxy-1,2,3,4-tetrahydro-naphthalen-2-yl)-propyl-amino]-methyl)-piperidin-1-yl)-morpholin-4-yl-methanone.

GENERAL SYNTHETIC REACTION SCHEMES

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser (1991) *Reagents for Organic Synthesis*; Wiley & Sons: New York, Volumes 1–15; Rodd (1989) *Chemistry of Carbon Compounds*, Elsevier Science Publishers, Volumes 1–5 and Supplementals; and (1991) *Organic Reactions*, Wiley & Sons: New York, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

SCHEME A

Scheme A, in general describes a method of preparing a compound of Formula I wherein $R^1$, $R^2$, $R^3$, A, and p are as described in the Summary of the invention.

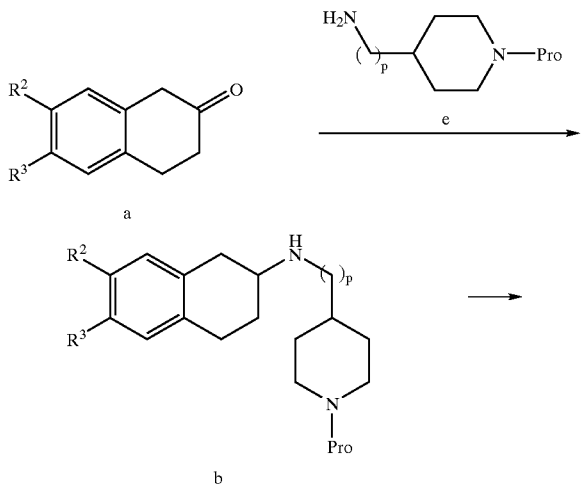

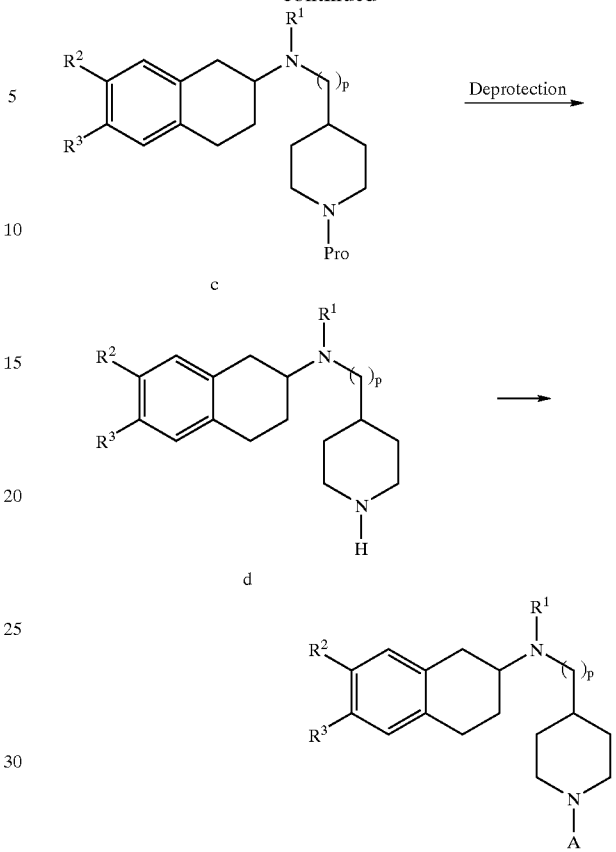

A compound of Formula b can generally be prepared by coupling a tetralone of Formula a with a protected amino piperidine of general Formula e under reductive amination conditions. Suitable reducing conditions include sodium triacetoxyborohydride, sodium cyanoborohydride, titanium isopropoxide and sodium cyanoborohydride, hydrogen and a metal catalyst, and hydrogen transfering agents such as cyclohexene, formic acid and its salts, zinc and hydrochloric acid formic acid, or borane sulfide followed by treatment with formic acid. Suitable organic solvents for the reaction include dichloromethane, 1,2-dichloroethane, tetrahydrofuran, alcohols or ethyl acetate, and the like. Preferably the reaction is carried out under basic conditions with sodium triacetoxyborohydride in 1,2-dichloroethane. Reductive amination procedures are described in the chemical literature. For example *J. Org. Chem.*, 1996, 61, 3849 and *Tetrahedron Letters*, 1996, 37, 3977, describe methods utilizing sodium triacetoxyborohydride as a reagent for the reductive amination of aldehydes with a wide variety of amines. A compound of Formula b is further coupled under reductive amination conditions as described herein with the appropriate carboxyaldehyde to generally give a compound of Formula c, which after deprotection of the piperidine group under conditions well known in the art as described herein, can undergo acylation, alkylation or sulfonation with an acid chloride $R^4C(O)Cl$, a carbamoyl chloride $R^4COCl$, an isocyanate $R^4CO$, or a sulfonyl chloride $R^5S(O)_2Cl$ respectively, wherein $R^4$ and $R^5$ are as described in the summary of the invention, under conditions well known in the art, to generally give a compound of Formula I.

The conventional starting materials of Scheme A are commercially available or are known to, or can readily be synthesized by those of ordinary skill in the art.

GENERAL UTILITY

Compounds that act as antagonists of muscarinic receptors have been used to treat several disease states associated with improper smooth muscle function. Until recently, most of these compounds have been non-selective for the various muscarinic receptor subtypes, leading to unpleasant anticholinergic side-effects such as dry mouth, constipation, blurred vision or tachycardia, the most common of which is dry-mouth that results from muscarinic receptor blockade in the salivary gland. Recently developed M2 and/or M3 specific antagonists have been shown to have reduced side effects. Evidence suggests that mechanistically, concurrent blockade of M2 and/or M3 receptors over M5 receptor could be therapeutically effective in the treatment of disease states associated with smooth muscle disorders, such as genitourinary tract disorders, respiratory tract disorders, gastrointestinal tract disorders, smooth muscle disorders, and cognitive and neurodegenerative disorders.

Genitourinary tract disorders treatable with compounds of this invention specifically include overactive bladder or detrusor hyperactivity and its symptoms such as the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

Gastrointestinal tract disorders treatable with compounds of this invention specifically include irritable bowel syndrome, diverticular disease, achalasia, gastrointestinal hypermotility disorders, and diarrhea.

Respiratory tract disorders treatable with compounds of this invention specifically include chronic obstructive pulmonary disease, including chronic bronchitis, emphysema, asthma and pulmonary fibrosis.

Compounds with selectivity for the M2 muscarinic receptor have also been shown to be useful in the treatment of cognitive and neurodegenerative diseases such as for example, Alzheimer's disease, as described in J. Med. Chem (1993), 36, 3734–3737. U.S. Pat. No. 6,294,554 describes muscarinic antagonists for the treatment of cognitive disorders.

These and other therapeutic uses are described, for example, in Goodman & Gilman, (1996) *The Pharmacological Basis of Therapeutics*, ninth edition, McGraw-Hill, New York, Chapter 26:601–616 and Coleman, R. A., (1994) *Pharmacological Reviews*, 46:205–229.

TESTING

The compounds of this invention are muscarinic receptor antagonists. The muscarinic receptor affinity of test compounds can be determined by an in vitro receptor binding assay which utilizes a cell membrane preparation from the Chinese hamster ovary cells expressing the recombinant human muscarinic receptors ($M_1$–$M_5$), and is described in more detail in Example 18.

The muscarinic antagonist properties of the test compounds can be identified by an in vivo assay which determines inhibitory activity against muscarinic receptor mediated saliva secretion in anesthetized rats, and is described in more detail in the Oxotremorine/Pilocarpine-induced salivation (OIS/PIS) model in anesthetized rats, Example 19.

The muscarinic antagonist properties of the test compounds can be identified by an in vivo assay which determines inhibitory activity against muscarinic receptor mediated bladder contraction in anesthetized rats, and is described in more detail in the inhibition of volume-induced contractions assay, Example 20.

The muscarinic antagonist properties of the test compounds can be identified by an in vivo assay which determines inhibitory activity against muscarinic receptor mediated bladder contraction and saliva secretion in anesthetized dogs, and is described in more detail in Example 21.

The muscarinic antagonist properties of the test compounds as anti-bronchoconstriction agents can be identified by an in vivo assay in anesthetized rats as described in more detail in Example 22.

ADMINISTRATION AND PHARMACEUTICAL COMPOSITION

The present invention includes pharmaceutical compositions comprising at least one compound of the present invention, or a prodrug, an individual isomer, a racemic or non-racemic mixture of isomers, or a pharmaceutically acceptable salt or solvate thereof together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease. In general, compounds of the present invention will be administered as pharmaceutical formulations including those suitable for oral (including buccal and sub-lingual), rectal, nasal, topical, pulmonary, vaginal, transdermal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically cceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion, or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents, or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing, and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

The compounds of the present invention can be formulated in transdermal or subcutaneous drug delivery devices. These delivery systems are advantageous when sustained release of the compound is necessary and when patient compliance with a treatment regimen is crucial. Compounds in a transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided

EXAMPLES

The following preparations and examples are given to enable those skilled in the art to more clearly understand and to practice the present invention. They should not be considered as limiting the scope of the invention, but merely as being illustrative and representative thereof.

Example 1

4-({Ethyl-[7-(4-methanesulfonyl-benzoylamino)-1,2,3,4-tetrahydro-naphthalen-2-yl]-amino}-methyl)-piperidine-1-carboxylic Acid Isopropylamide

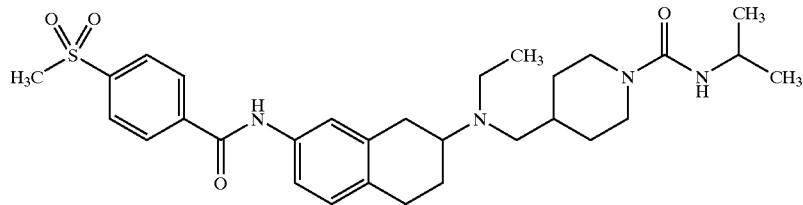

Step 1:
4-[(7-Nitro-1,2,3,4-tetrahydro-naphthalen-2-ylamino)-methyl]-piperidine-1-carboxylic Acid tert-Butyl Ester

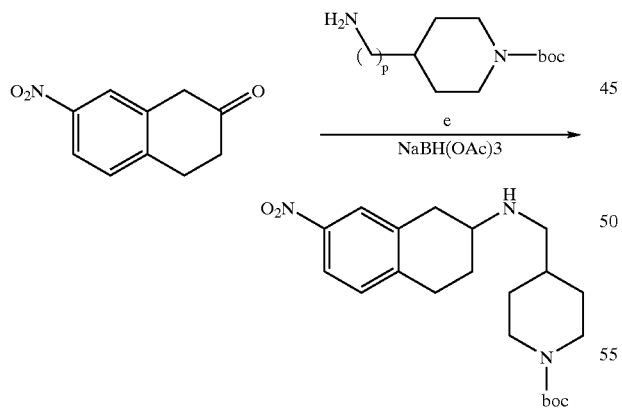

To a solution of 7-nitro-3,4-dihydro-1H-naphthalen-2-one (600 mg, 2.98 mmol), prepared as described in *J. Med. Chem.*, 1989, 32(9), 2128–34, and 4-aminomethyl-piperidine-1-carboxylic acid tert-butyl ester (700 mg, 3.3 mmol) in dichloroethane (50 mL) under a nitrogen atmosphere was added sodium triacetoxyborohydride (1.4 g, 6.5 mmol, 2 eq.) in a single portion. The reaction was stirred at room temperature for 24 h. The reaction was concentrated in vacuo and partitioned between EtOAc (100 mL) and 5% aq. KOH (50 mL). The aqueous layer was extracted twice more with EtOAc (2×50 mL). The combined organic layers were washed with brine, dried over MgSO$_4$, filtered, and concentrated to afford a dark oil. Flash chromatography on silica gel eluting with 5% methanol/methylene chloride afforded 4-[(7-nitro-1,2,3,4-tetrahydro-naphthalen-2-ylamino)-methyl]-piperidine-1-carboxylic acid tert-butyl ester, as an oil (790 mg).

Step 2:

4-{[Ethyl-(7-nitro-1,2,3,4-tetrahydro-naphthalen-2-yl)-amino]-methyl}-piperidine-1-carboxylic Acid tert-Butyl Ester

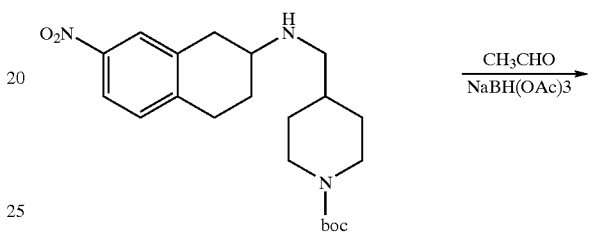

-continued

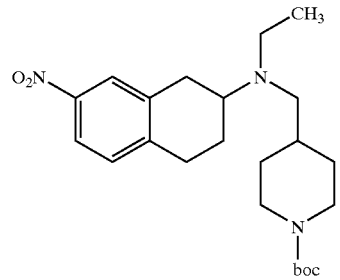

To a solution of 4-[(7-nitro-1,2,3,4-tetrahydro-naphthalen-2-ylamino)-methyl]-piperidine-1-carboxylic acid tert-butyl ester (485 mg, 1.25 mmol) and acetaldehyde (110 µL, 1.49 mmol) in dichloroethane (20 mL) under a nitrogen atmosphere was added sodium triacetoxyborohydride (530 mg, 2.49 mmol, 2 eq.) in a single portion. The reaction was stirred at room temperature for 24 h then concentrated in vacuo. The residue was partitioned between EtOAc (75 mL) and 5% aq. KOH (50 mL). The aqueous phase was extracted twice more with EtOAc (2×30 mL). The combined organic layers were dried over MgSO$_4$, filtered, and concentrated onto silica (10 g). This was placed on top of a flash column and eluted with 20% acetone in hexanes. The fractions containing product were pooled and concentrated to afford 4-{[ethyl-(7-nitro-1,2,3,4-tetrahydro-naphthalen-2-yl)-amino]-methyl}-piperidine-1-carboxylic acid tert-butyl ester as a yellow oil (430 mg).

Step 3:
4-{[(7-Amino-1,2,3,4-tetrahydro-naphthalen-2-yl)-ethyl-amino]-methyl}-piperidine-1-carboxylic Acid tert-Butyl Ester

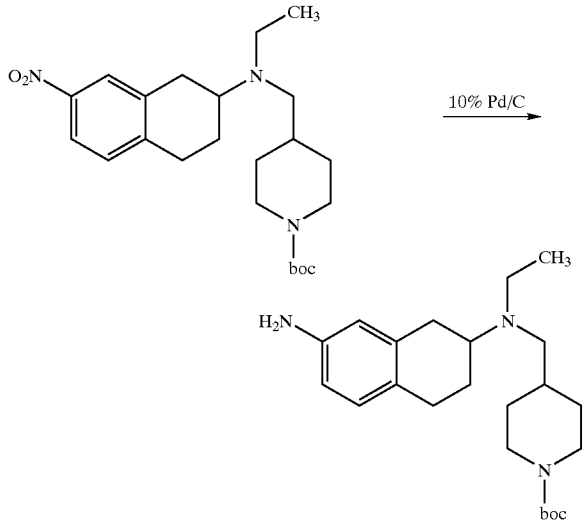

To a solution of 4-{[ethyl-(7-nitro-1,2,3,4-tetrahydro-naphthalen-2-yl)-amino]-methyl}-piperidine-1-carboxylic acid tert-butyl ester (490 mg, 1.2 mmol) in ethanol (30 mL) was added 10% palladium on charcoal (50 mg). The solution was shaken on a Parr shaker for 24 h at 55 psi of hydrogen. The solution was filtered through Celite® and concentrated to afford 4-{[(7-amino-1,2,3,4-tetrahydro-naphthalen-2-yl)-ethyl-amino]-methyl}-piperidine-1-carboxylic acid tert-butyl ester as an oil (405 mg) which was used directly.

Step 4:
4-({Ethyl-[7-(4-methanesulfonyl-benzoylamino)-1,2,3,4-tetrahydro-naphthalen-2-yl]-amino}-methyl)-piperidine-1-carboxylic Acid tert-Butyl Ester

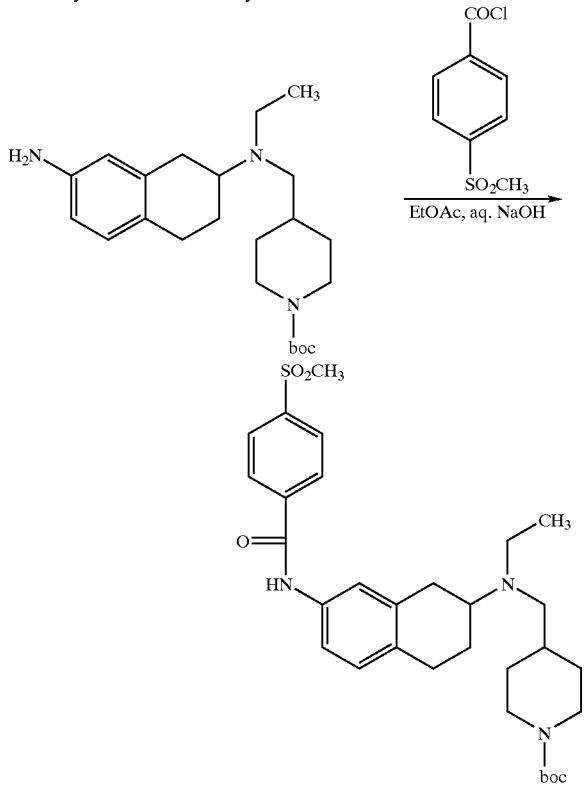

To a solution of 4-{[(7-amino-1,2,3,4-tetrahydro-naphthalen-2-yl)-ethyl-amino]-methyl}-piperidine-1-carboxylic acid tert-butyl ester (1.5 g, 3.87 mmol) in EtOAc (50 mL) and 20% aq. potassium carbonate (50 mL) was added 4-methanesulfonyl-benzoyl chloride (760 mg, 4.1 mmol) dropwise in EtOAc (75 mL). The reaction was stirred at room temperature overnight and the layers separated. The EtOAc layer was concentrated onto silica gel and placed on top of a flash column. The column was eluted with 35% acetone in hexanes. Product containing fractions were pooled and concentrated to afford 4-({ethyl-[7-(4-methanesulfonyl-benzoylamino)-1,2,3,4-tetrahydro-naphthalen-2-yl]-amino}-methyl)-piperidine-1-carboxylic acid tert-butyl ester as a light pink solid (1.33 g).

Step 5:
N-[7-(Ethyl-piperidin-4-ylmethyl-amino)-5,6,7,8-tetrahydro-naphthalen-2-yl]-4-methanesulfonyl-benzamide

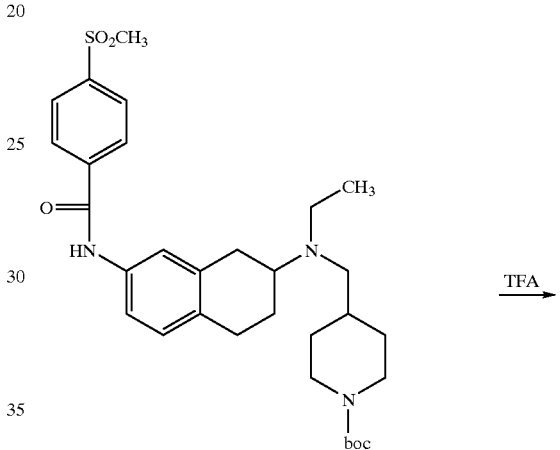

To a solution of 4-({ethyl-[7-(4-methanesulfonyl-benzoylamino)-1,2,3,4-tetrahydro-naphthalen-2-yl]-amino}-methyl)-piperidine-1-carboxylic acid tert-butyl ester (1.33 g, 2.3 mmol) in methylene chloride (30 mL) under a nitrogen atmosphere was added trifluoroacetic acid (10 mL). The reaction was stirred at room temperature for 30 min. and concentrated in-vacuo. The residue was partitioned between EtOAc (50 mL) and 10% aq. KOH (50 mL), the organic layer was separated, dried over MgSO$_4$, filtered, and concentrated to afford N-[7-(ethyl-piperidin-4-ylmethyl-amino)-5,6,7,8-tetrahydro-naphthalen-2-yl]-4-methanesulfonyl-benzamide (1.02 g). [M+H]$^+$=470.

Step 6:
4-({Ethyl-[7-(4-methanesulfonyl-benzoylamino)-1,2,3,4-tetrahydro-naphthalen-2-yl]-amino}-methyl)-piperidine-1-carboxylic Acid Isopropylamide

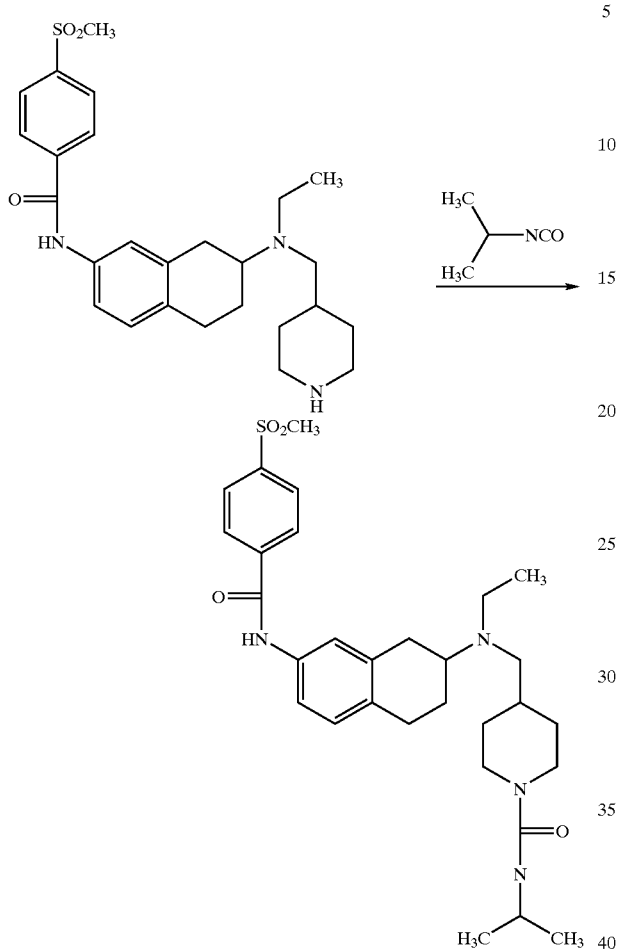

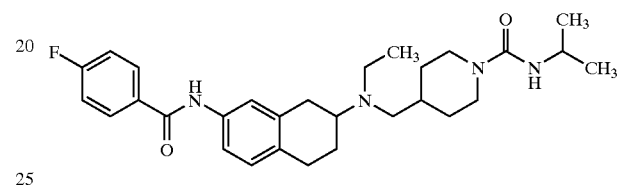

To an ice-cold solution of N-[7-(ethyl-piperidin-4-ylmethyl-amino)-5,6,7,8-tetrahydro-naphthalen-2-yl]-4-methanesulfonyl-benzamide (1.3 g, 2.3 mmol) in methylene chloride (40 mL) under a nitrogen atmosphere was added the triethylamine (1.3 mL, 9.2 mmol, 4 eq.) in a single portion followed by the isopropylisocyanate (0.33 mL, 3.3 mmol, 1.4 eq). The reaction was allowed to warm to room temperature and stirred for 24 h. The reaction was concentrated in vacuo and partitioned between EtOAc (75 mL) and 10% aq. sodium hydroxide (40 mL). The aqueous layer was extracted with EtOAc (2×30 mL) and the combined EtOAc layers were dried over MgSO$_4$, filtered, and concentrated. Trituration with ether afforded 4-({ethyl-[7-(4-methanesulfonyl-benzoylamino)-1,2,3,4-tetrahydro-naphthalen-2-yl]-amino}-methyl)-piperidine-1-carboxylic acid isopropylamide 1 as a light pink solid (1.1 g). [M+H]$^+$=555.

Similarly following the procedure described above in Example 1, but replacing in Step 6 isopropylisocyanate with other appropriate isocyanates, the following compounds were prepared:

N-(7-{ethyl-[1-(morpholine-4-carbonyl)-piperidin-4-ylmethyl]-amino}-5,6,7,8-tetrahydro-naphthalen-2-yl)-4-methanesulfonyl-benzamide 2, [M+H]$^+$=583;

4-({ethyl-[7-(4-methanesulfonyl-benzoylamino)-1,2,3,4-tetrahydro-naphthalen-2-yl]-amino}-methyl)-piperidine-1-carboxylic acid diethylamide 3, [M+H]$^+$=569;

4-({ethyl-[7-(4-methanesulfonyl-benzoylamino)-1,2,3,4-tetrahydro-naphthalen-2-yl]-amino}-methyl)-piperidine-1-carboxylic acid methylamide 4, [M+H]$^+$=527;

4-({ethyl-[7-(4-methanesulfonyl-benzoylamino)-1,2,3,4-tetrahydro-naphthalen-2-yl]-amino}-methyl)-piperidine-1-carboxylic acid phenylamide 5, [M+H]$^+$=589; and 4-({ethyl-[7-(4-methanesulfonyl-benzoylamino)-1,2,3,4-tetrahydro-naphthalen-2-yl]-amino}-methyl)-piperidine-1-carboxylic acid amide 6, [M+H]$^+$=513.

Example 2

4-({Ethyl-[7-(4-fluoro-benzoylamino)-1,2,3,4-tetrahydro-naphthalen-2-yl]-amino}-methyl)-piperidine-1-carboxylic Acid Isopropylamide

Step 1:
4-({Ethyl-[7-(2,2,2-trifluoro-acetylamino)-1,2,3,4-tetrahydro-naphthalen-2-yl]-amino}-methyl)-piperidine-1-carboxylic Acid tert-Butyl Ester

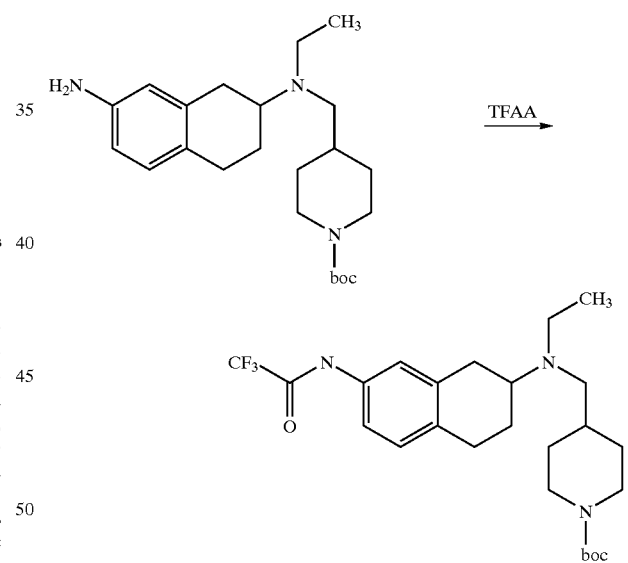

To a stirring solution of 4-{[(7-amino-1,2,3,4-tetrahydro-naphthalen-2-yl)-ethyl-amino]-methyl}-piperidine-1-carboxylic acid tert-butyl ester (2.3 g, 5.36 mmol) in methylene chloride (30 mL) under an inert atmosphere was added pyridine (0.9 mL, 10.7 mmol) and trifluoroacetic anhydride (1.0 ml, 6.96 mmol) and the solution was allowed to stir at room temperature for 20 h. The reaction was concentrated in vacuo and partitioned between EtOAc and water. The organic layer was washed with brine, dried (MgSO$_4$), and concentrated. The crude reaction product was flash chromatographed on silica eluting with 20% acetone in hexanes to afford 4-({ethyl-[7-5 (2,2,2-trifluoro-acetylamino)-1,2,3,4-tetrahydro-naphthalen-2-yl]-amino}-methyl)-piperidine-1-carboxylic acid tert-butyl ester as an orange oil (1.2 g).

Step 2:
N-[7-(Ethyl-piperidin-4-ylmethyl-amino)-5,6,7,8-tetrahydro-naphthalen-2-yl]-2,2,2-trifluoro-acetamide

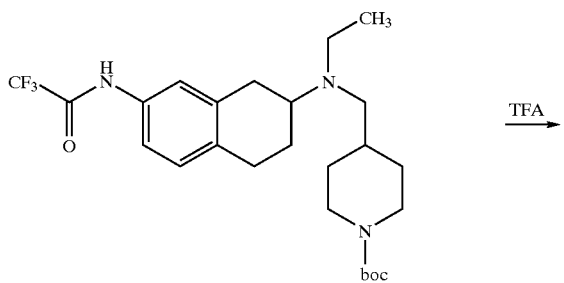

To a solution of the 4-({ethyl-[7-(2,2,2-trifluoro-acetylamino)-1,2,3,4-tetrahydro-naphthalen-2-yl]-amino}-methyl)-piperidine-1-carboxylic acid tert-butyl ester (800 mg, 1.7 mmol) in methylene chloride (20 mL) under an inert atmosphere was added trifluoroacetic acid (5 mL) and the solution was allowed to stir at room temperature for 1 h. The reaction was concentrated in vacuo and partitioned between 10% KOH and EtOAc. The organic layer was washed with brine, dried (MgSO₄), and concentrated to afford N-[7-(ethyl-piperidin-4-ylmethyl-amino)-5,6,7,8-tetrahydro-naphthalen-2-yl]-2,2,2-trifluoro-acetamide as an oil which was used directly for the next step.

Step 3:
4-({Ethyl-[7-(2,2,2-trifluoro-acetylamino)-1,2,3,4-tetrahydro-naphthalen-2-yl]-amino}-methyl)-piperidine-1-carboxylic Acid Isopropylamide

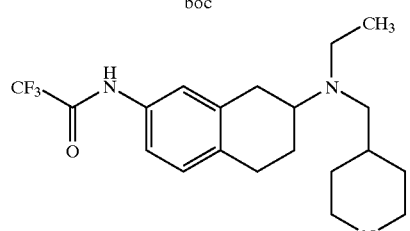

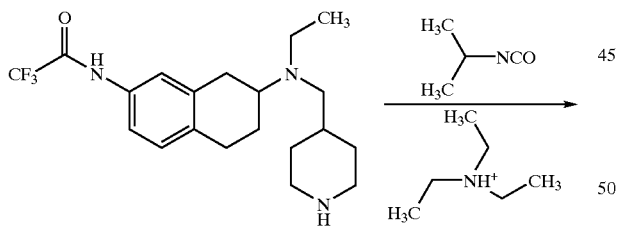

To a solution of N-[7-(ethyl-piperidin-4-ylmethyl-amino)-5,6,7,8-tetrahydro-naphthalen-2-yl]-2,2,2-trifluoro-acetamide (1.7 mmol) in methylene chloride (20 mL) under an inert atmosphere was added triethylamine (1.0 mL, 6.6 mmol) and isopropyl isocyanate (230 μL, 2.3 mmol). The reaction was stirred for 20 h and then concentrated in vacuo. This material was partitioned between 5% KOH and water. The organic layer was dried (MgSO₄) and concentrated to afford 4-({ethyl-[7-(2,2,2-trifluoro-acetylamino)-1,2,3,4-tetrahydro-naphthalen-2-yl]-amino}-methyl)-piperidine-1-carboxylic acid isopropylamide as a clear oil (630 mg).

Step 4:

4-{[(7-Amino-1,2,3,4-tetrahydro-naphthalen-2-yl)-ethyl-amino]-methyl}-piperidine-1-carboxylic Acid Isopropylamide

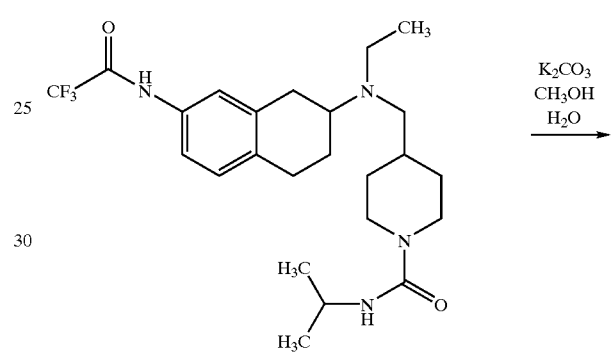

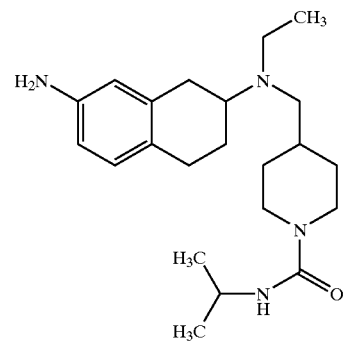

To a solution of the 4-({ethyl-[7-(2,2,2-trifluoro-acetylamino)-1,2,3,4-tetrahydro-naphthalen-2-yl]-amino}-methyl)-piperidine-1-carboxylic acid isopropylamide (630 mg, 1.3 mmol) in methanol (20 mL) and water (10 mL) was added potassium carbonate (500 mg) and the reaction was allowed to stir at room temperature for 24 h. The reaction was concentrated in vacuo and partitioned between EtOAc and water. The organic layer was washed with brine, dried (MgSO₄) and concentrated to afford 4-{[(7-amino-1,2,3,4-tetrahydro-naphthalen-2-yl)-ethyl-amino]-methyl}-piperidine-1-carboxylic acid isopropylamide as a light brown oil (464 mg).

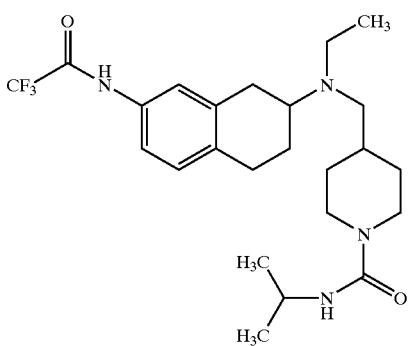

Step 5:
4-({Ethyl-[7-(4-fluoro-benzoylamino)-1,2,3,4-tetrahydro-naphthalen-2-yl]-amino}-methyl)-piperidine-1-carboxylic Acid Isopropylamide

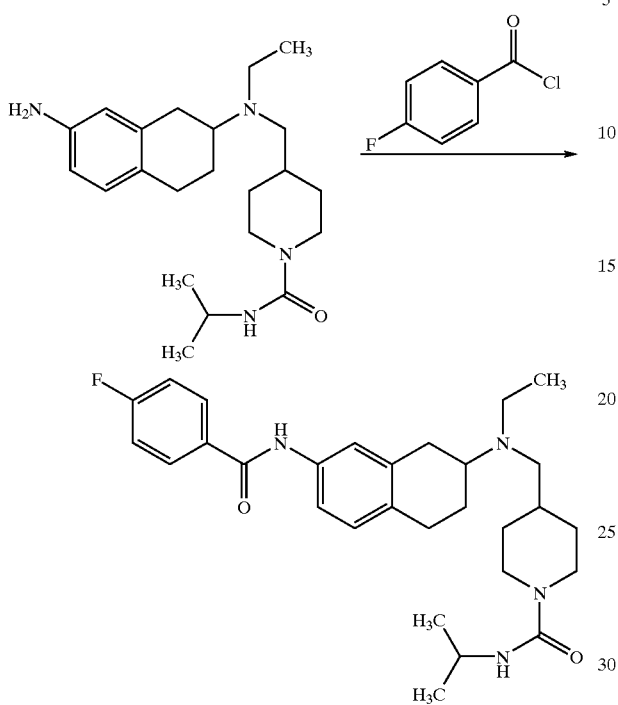

To a solution of 4-{[(7-amino-1,2,3,4-tetrahydro-naphthalen-2-yl)-ethyl-amino]-methyl}-piperidine-1-carboxylic acid isopropylamide (200 µL of 0.25 M in acetonitrile, 50 µmol) was added 220 µL of a 0.25 M solution of 4-fluorobenzoyl chloride in dichloromethane and 30 µL of DIEA. The solution was allowed to stir for 24 h at 25° C. under N₂ and concentrated in vacuo. The final product was isolated by preparative RPHPLC (YMC Combiprep ODS-A column, 10–90% acetonitrile:water (0.1% TFA)) to afford 4-({ethyl-[7-(4-fluoro-benzoylamino)-1,2,3,4-tetrahydro-naphthalen-2-yl]-amino}-methyl)-piperidine-1-carboxylic acid isopropylamide (13.1 mg) 7 [M+H]⁺=495.

Similarly following the procedure described above in Example 2, Step 5, but replacing 4-fluorobenzoyl chloride with the appropriate acid chloride or sulfonyl chloride, the following compounds were prepared:

4-({ethyl-[7-(4-trifluoromethyl-benzoylamino methyl)-piperidine-1-carboxylic)-1,2,3,4-tetrahydro-naphthalen-2-yl]-amino}-methyl)-piperidine-1-carboxylic acid isopropylamide 8, [M+H]⁺=545;

4-[(ethyl-{7-[(naphthalene-2-carbonyl)-amino]-1,2,3,4-tetrahydro-naphthalen-2-yl}-amino)-methyl]-piperidine-1-carboxylic acid isopropylamide 9, [M+H]⁺=527;

4-({ethyl-[7-(4-methoxy-benzoylamino)-1,2,3,4-tetrahydro-naphthalen-2-yl]-amino}-methyl)-piperidine-1-carboxylic acid isopropylamide 10, [M+H]⁺=507;

4-[({7-[(biphenyl-4-carbonyl)-amino]-1,2,3,4-tetrahydro-naphthalen-2-yl}-ethyl-amino)-methyl]-piperidine-1-carboxylic acid isopropylamide 11, [M+H]⁺=553;

4-{[(7-diphenylacetylamino-1,2,3,4-tetrahydro-naphthalen-2-yl)-ethyl-amino]-methyl}-piperidine-1-carboxylic acid isopropylamide 12, [M+H]⁺=567;

4-({ethyl-[7-(2-phenyl-butyrylamino)-1,2,3,4-tetrahydro-naphthalen-2-yl]-amino}-methyl)-piperidine-1-carboxylic acid isopropylamide 13, [M+H]⁺=519;

4-[(ethyl-{7-[2-(4-methoxy-phenyl)-acetylamino]-1,2,3,4-tetrahydro-naphthalen-2-yl}-amino)-methyl]-piperidine-1-carboxylic acid isopropylamide 14, [M+H]⁺=521;

4-({[7-(4-dimethylamino-benzoylamino)-1,2,3,4-tetrahydro-naphthalen-2-yl]-ethyl-amino}-methyl)-piperidine-1-carboxylic acid isopropylamide 15, [M+H]⁺=520;

4-({[7-(2,4-difluoro-benzoylamino)-1,2,3,4-tetrahydro-naphthalen-2-yl]-ethyl-amino}-methyl)-piperidine-1-carboxylic acid isopropylamide 16, [M+H]⁺=513;

4-({ethyl-[7-(naphthalene-2-sulfonylamino)-1,2,3,4-tetrahydro-naphthalen-2-yl]-amino}-methyl)-piperidine-1-carboxylic acid isopropylamide 17, [M+H]⁺=563;

4-({ethyl-[7-(4-methoxy-benzenesulfonylamino)-1,2,3,4-tetrahydro-naphthalen-2-yl]-amino}-methyl)-piperidine-1-carboxylic acid isopropylamide 18, [M+H]⁺=543;

4-{[ethyl-(7-phenylmethanesulfonylamino-1,2,3,4-tetrahydro-naphthalen-2-yl)-amino]-methyl}-piperidine-1-carboxylic acid isopropylamide 19, [M+H]⁺=527;

4-({ethyl-[7-(4-trifluoromethoxy-benzenesulfonyl-amino)-1,2,3,4-tetrahydro-naphthalen-2-yl]-amino}-methyl)-piperidine-1-carboxylic acid isopropylamide20, [M+H]⁺=597;

4-({ethyl-[7-(4-fluoro-benzenesulfonylamino)-1,2,3,4-tetrahydro-naphthalen-2-yl]-amino}-methyl)-piperidine-1-carboxylic acid isopropylamide 21, [M+H]⁺=531;

4-({ethyl-[7-(4-trifluoromethyl-benzenesulfonylamino)-1,2,3,4-tetrahydro-naphthalen-2-yl]-amino}-methyl)-piperidine-1-carboxylic acid isopropylamide 22, [M+H]⁺=531;

4-({[7-(biphenyl-4-sulfonylamino)-1,2,3,4-tetrahydro-naphthalen-2-yl]-ethyl-amino)-methyl)-piperidine-1-carboxylic acid isopropylamide 23, [M+H]⁺=589; and 4-[(ethyl-{7-[2-(4-isobutyl-phenyl)-propionylamino]-1,2,3,4-tetrahydro-naphthalen-2-yl}-amino)-methyl]-piperidine-1-carboxylic acid isopropylamide 24, [M+H]⁺=589.

Example 3

4-{[(7-Methoxy-1,2,3,4-tetrahydro-naphthalen-2-yl)-propyl-amino]-methyl}-piperidine-1-carboxylic Acid Methylamide

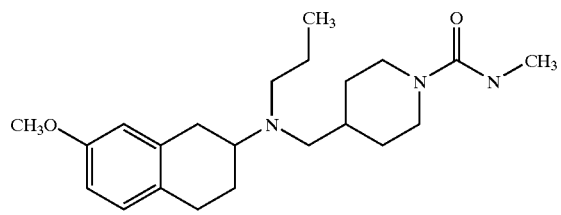

Step 1:
4-[(7-Methoxy-1,2,3,4-tetrahydro-naphthalen-2-ylamino)-methyl}-piperidine-1-carboxylic Acid tert-Butyl Ester

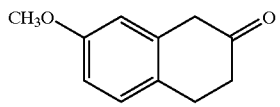

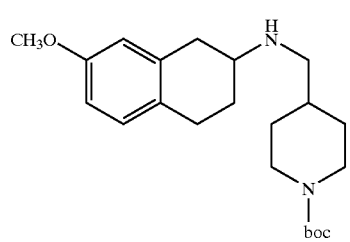

To a solution of 7-methoxy-3,4-dihydro-1H-naphthalen-2-one (1.0 g, 5.67 mmol) and 4-aminomethyl-piperidine-1-carboxylic acid tert-butyl ester (1.34 g, 6.23 mmol) in dichloroethane (50 mL) under a nitrogen atmosphere was added sodium triacetoxyborohydride (3.0 g, 14.2 mmol, 2.5 eq.) in a single portion. The reaction was stirred at room temperature for 24 h. The reaction was concentrated in vacuo and partitioned between EtOAc (100 mL) and 5% aq. KOH (50 mL). The aqueous layer was extracted twice more with ethyl acetate (2×50 mL). The combined organic layers were washed with brine, dried over MgSO$_4$, filtered, and concentrated. Flash chromatography on silica gel eluting with 5% methanol/methylene chloride afforded 4-[(7-methoxy-1,2,3,4-tetrahydro-naphthalen-2-ylamino)-methyl]-piperidine-1-carboxylic acid tert-butyl ester as an oil (2.1 g).

Step 2:
4-{[(7-Methoxy-1,2,3,4-tetrahydro-naphthalen-2-vl)-propyl-amino]-methyl}-piperidine-1-carboxylic Acid Tert-Butyl Ester

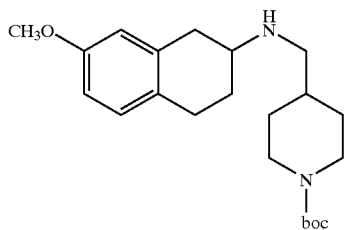

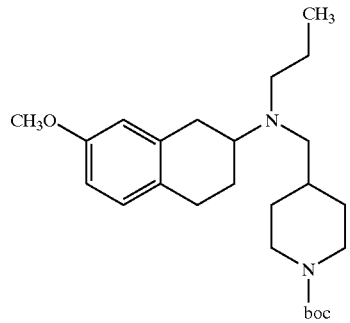

To a solution of 4-[(7-methoxy-1,2,3,4-tetrahydro-naphthalen-2-ylamino)-methyl]-piperidine-1-carboxylic acid tert-butyl ester (2.1 g, 5.6 mmol) and propionaldehyde (0.45 mL, 6.23 mmol) in dichloroethane (20 mL) under a nitrogen atmosphere was added sodium triacetoxyborohydride (3.09 g, 14.15 mmol, 2.5 eq.) in a single portion. The reaction was stirred at room temperature for 24 h then concentrated in vacuo. The residue was partitioned between EtOAc (75 mL) and 5% aq. KOH (50 mL). The aqueous phase was extracted twice more with EtOAc (2×30 mL). The combined organic layers were dried over MgSO$_4$, filtered, and concentrated onto silica (10 g). This was placed on top of a flash column and eluted with 20% acetone in hexanes. The fractions containing product were pooled and concentrated to afford 4-{[(7-methoxy-1,2,3,4-tetrahydro-naphthalen-2-yl)-propyl-amino]-methyl}-piperidine-1-carboxylic acid tert-butyl ester (2.4 g).

Step 3:
(7-Methoxy-1,2,3,4-tetrahydro-naphthalen-2-yl)-piperidin-4-ylmethyl-propyl-amine

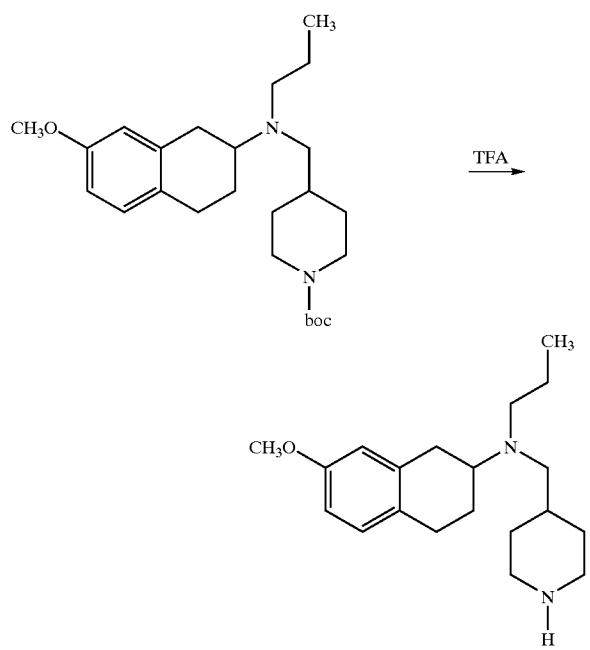

To a solution of 4-{[(7-methoxy-1,2,3,4-tetrahydro-naphthalen-2-yl)-propyl-amino]-methyl}-piperidine-1-carboxylic acid tert-butyl ester (2.4 g, 4.56 mmol) in methylene chloride (30 mL) under a nitrogen atmosphere was added trifluoroacetic acid (10 mL). The reaction was stirred at room temperature for 30 min. and concentrated in vacuo. The residue was partitioned between EtOAc (50 mL) and 10% aq. KOH (50 mL). The organic layer was separated, dried over MgSO$_4$, filtered, and concentrated to afford (7-methoxy-1,2,3,4-tetrahydro-naphthalen-2-yl)-piperidin-4-ylmethyl-propyl-amine (1.62 g).

Step 4:
4-{[(7-Methoxy-1,2,34-tetrahydro-naphthalen-2-yl)-propyl-amino]-methyl}-piperidine-1-carboxylic Acid Methylamide

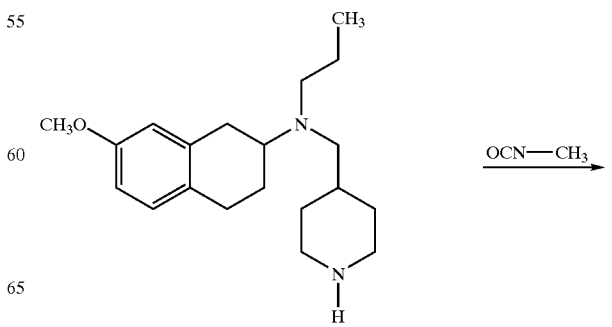

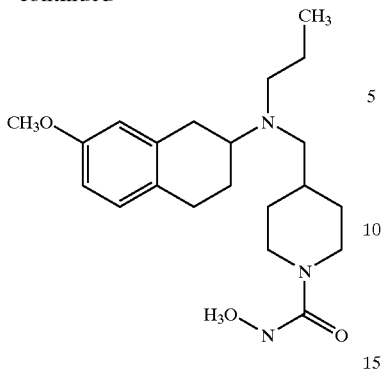

To a solution of (7-methoxy-1,2,3,4-tetrahydro-naphthalen-2-yl)-piperidin-4-ylmethyl-propyl-amine (200 μL of a 0.25 M solution in dichloromethane, 50 μmole) was added 220 μL of a 0.25 M solution of methyl isocyanate in acetonitrile and 30 μL of DIEA. The solution was allowed to stir for 24 h at 25° C. under $N_2$ and then concentrated in vacuo. The final product was isolated by preparative RPHPLC (YMC Combiprep ODS-A column, 10–90% acetonitrile: water (0.1% TFA)) to afford 4-{[(7-methoxy-1,2,3,4-tetrahydro-naphthalen-2-yl)-propyl-amino]-methyl}-piperidine-1-carboxylic acid methylamide (17.1 mg) 25 $[M+H]^+$=374.

Similarly following the procedure described above in Example 3, Step 4, but replacing methyl isocyanate with the appropriate isocyanate, sulfonyl chloride, carbamoyl chloride, or acid chloride the following compounds were prepared:

4-{[(7-methoxy-1,2,3,4-tetrahydro-naphthalen-2-yl)-propyl-amino]-methyl}-piperidine-1-carboxylic acid adamantan-1-ylamide 26, $[M+H]^+$=494;

4-{[(7-methoxy-1,2,3,4-tetrahydro-naphthalen-2-yl)-propyl-amino]-methyl}-piperidine-1-carboxylic acid isopropylamide 27, $[M+H]^+$=402;

(4-{[(7-methoxy-1,2,3,4-tetrahydro-naphthalen-2-yl)-propyl-amino]-methyl}-piperidin-1-yl)-morpholin-4-yl-methanone 28, $[M+H]^+$=430;

4-{[(7-methoxy-1,2,3,4-tetrahydro-naphthalen-2-yl)-propyl-amino]-methyl}-piperidine-1-carboxylic acid diethylamide 29, $[M+H]^+$=416;

4-{[(7-methoxy-1,2,3,4-tetrahydro-naphthalen-2-yl)-propyl-amino]-methyl}-piperidine-1-carboxylic acid diisopropylamide 30, $[M+H]^+$=444;

(4-{[(7-methoxy-1,2,3,4-tetrahydro-naphthalen-2-yl)-propyl-amino]-methyl}-piperidin-1-yl)-pyrrolidin-1-yl-methanone 31, $[M+H]^+$=414;

4-{[(7-methoxy-1,2,3,4-tetrahydro-naphthalen-2-yl)-propyl-amino]-methyl}-piperidine-1-carboxylic acid dimethylamide 32, $[M+H]^+$=388;

4-{[(7-methoxy-1,2,3,4-tetrahydro-naphthalen-2-yl)-propyl-amino]-methyl}-piperidine-1-carboxylic acid methyl-phenyl-amide 33, $[M+H]^+$=450;

(1-benzenesulfonyl-piperidin-4-ylmethyl)-(7-methoxy-1,2,3,4-tetrahydro-naphthalen-2-yl)-propyl-amine 34, $[M+H]^+$=457;

(1-methanesulfonyl-piperidin-4-ylmethyl)-(7-methoxy-1,2,3,4-tetrahydro-naphthalen-2-yl)-propyl-amine 35, $[M+H]^+$=395;

7-methoxy-1,2,3,4-tetrahydro-naphthalen-2-yl)-[1-(propane-2-sulfonyl)-piperidin-4-ylmethyl]-propyl-amine 36, $[M+H]^+$=423;

[1-(2-chloro-benzenesulfonyl)-piperidin-4-ylmethyl]-(7-methoxy-1,2,3,4-tetrahydro-naphthalen-2-yl)-propyl-amine 37, $[M+H]^+$=491;

(7-methoxy-1,2,3,4-tetrahydro-naphthalen-2-yl)-[1-(1-methyl-1H-imidazole-4-sulfonyl)-piperidin-4-ylmethyl]-propyl-amine 38, $[M+H]^+$=461;

1-(4-{[(7-methoxy-1,2,3,4-tetrahydro-naphthalen-2-yl)-propyl-amino]-methyl}-piperidin-1-yl)-2,2-dimethyl-propan-1-one 39, $[M+H]^+$=401;

1-(4-{[(7-methoxy-1,2,3,4-tetrahydro-naphthalen-2-yl)-propyl-amino]-methyl}-piperidin-1-yl)-3-methyl-butan-1-one 40, $[M+H]^+$=401;

(4-{[(7-methoxy-1,2,3,4-tetrahydro-naphthalen-2-yl)-propyl-amino]-methyl}-piperidin-1-yl)-thiophen-2-yl-methanone 41, $[M+H]^+$=427;

Isoxazol-5-yl-(4-{[(7-methoxy-1,2,3,4-tetrahydro-naphthalen-2-yl)-propyl-amino]-methyl}-piperidin-1-yl)-methanone 42, $[M+H]^+$=412;

1-(4-{[(7-methoxy-1,2,3,4-tetrahydro-naphthalen-2-yl)-propyl-amino]-methyl}-piperidin-1-yl)-2,2-diphenyl-ethanone 43, $[M+H]^+$=511;

1-(4-{[(7-methoxy-1,2,3,4-tetrahydro-naphthalen-2-yl)-propyl-amino]-methyl}-piperidin-1-yl)-ethanone 44, $[M+H]^+$=359; and (1-methanesulfonyl-piperidin-4-yl)-(4-{[(7-methoxy-1,2,3,4-tetrahydro-naphthalen-2-yl)-propyl-amino]-methyl}-piperidin-1-yl)-methanone 45, $[M+H]^+$=506.

Similarly following the procedure described above in Example 3, but replacing 7-methoxy-3,4-dihydro-1H-naphthalen-2-one with 6-methoxy-3,4-dihydro-1H-naphthalen-2-one in Step 1 and using the appropriate acid chlorides, sulfonyl chlorides, carbamoyl chlorides, or isocyanates in Step 4, the following compounds were prepared:

4-{[(6-methoxy-1,2,3,4-tetrahydro-naphthalen-2-yl)-propyl-amino]-methyl}-piperidine-1-carboxylic acid adamantan-1-ylamide 46, $[M+H]^+$=494;

4-{[(6-methoxy-1,2,3,4-tetrahydro-naphthalen-2-yl)-propyl-amino]-methyl}-piperidine-1-carboxylic acid (2-chloro-phenyl)-amide 47, $[M+H]^+$=470;

4-{[(6-methoxy-1,2,3,4-tetrahydro-naphthalen-2-yl)-propyl-amino]-methyl}-piperidine-1-carboxylic acid tert-butylamide 48, $[M+H]^+$=416;

4-{[(6-methoxy-1,2,3,4-tetrahydro-naphthalen-2-yl)-propyl-amino]-methyl}-piperidine-1-carboxylic acid isopropylamide 49, $[M+H]^+$=402;

4-{[(6-methoxy-1,2,3,4-tetrahydro-naphthalen-2-yl)-propyl-amino]-methyl}-piperidine-1-carboxylic acid methylamide 50, $[M+H]^+$=374;

(4-{[(6-methoxy-1,2,3,4-tetrahydro-naphthalen-2-yl)-propyl-amino]-methyl}-piperidin-1-yl)-morpholin-4-yl-methanone 51, $[M+H]^+$=430;

4-{[(6-methoxy-1,2,3,4-tetrahydro-naphthalen-2-yl)-propyl-amino]-methyl}-piperidine-1-carboxylic acid diethylamide 52, $[M+H]^+$=416;

4-{[(6-methoxy-1,2,3,4-tetrahydro-naphthalen-2-yl)-propyl-amino]-methyl}-piperidine-1-carboxylic acid diisopropylamide 53, $[M+H]^+$=444;

(4-{[(6-methoxy-1,2,3,4-tetrahydro-naphthalen-2-yl)-propyl-amino]-methyl}-piperidin-1-yl)-pyrrolidin-1-yl-methanone 54, $(M+H)^+$=414;

4-{[(6-methoxy-1,2,3,4-tetrahydro-naphthalen-2-yl)-propyl-amino]-methyl}-piperidine-1-carboxylic acid dimethylamide 55, $[M+H]^+$=388;

4-{[(6-methoxy-1,2,3,4-tetrahydro-naphthalen-2-yl)-propyl-amino]-methyl}-piperidine-1-carboxylic acid methyl-phenyl-amide 56, $[M+H]^+$=450;

(1-benzenesulfonyl-piperidin-4-ylmethyl)-(6-methoxy-1,2,3,4-tetrahydro-naphthalen-2-yl)-propyl-amine 57, [M+H]⁺=457;

(1-methanesulfonyl-piperidin-4-ylmethyl)-(6-methoxy-1,2,3,4-tetrahydro-naphthalen-2-yl)-propyl-amine 58, [M+H]⁺=395;

(6-methoxy-1,2,3,4-tetrahydro-naphthalen-2-yl)-[1-(propane-2-sulfonyl)-piperidin-4-ylmethyl]-propyl-amine 59, [M+H]⁺=423;

[1-(2-chloro-benzenesulfonyl)-piperidin-4-ylmethyl]-(6-methoxy-1,2,3,4-tetrahydro-naphthalen-2-yl)-propyl-amine 60, [M+H]⁺=491;

(6-methoxy-1,2,3,4-tetrahydro-naphthalen-2-yl)-[1-(1-methyl-1H-imidazole-4-sulfonyl)-piperidin-4-ylmethyl]-propyl-amine 61, [M+H]⁺=461;

1-(4-{[(6-methoxy-1,2,3,4-tetrahydro-naphthalen-2-yl)-propyl-amino]-methyl}-piperidin-1-yl)-2,2-dimethyl-propan-1-one 62, [M+H]⁺=401;

1-(4-{[(6-methoxy-1,2,3,4-tetrahydro-naphthalen-2-yl)-propyl-amino]-methyl}-piperidin-1-yl)-3-methyl-butan-1-one 63, [M+H]⁺=401;

(4-{[(6-methoxy-1,2,3,4-tetrahydro-naphthalen-2-yl)-propyl-amino]-methyl}-piperidin-1-yl)-thiophen-2-yl-methanone 64, [M+H]⁺=427;

isoxazol-5-yl-(4-{[(6-methoxy-1,2,3,4-tetrahydro-naphthalen-2-yl)-propyl-amino]-methyl}-piperidin-1-yl)-methanone 65, [M+H]⁺=412;

1-(4-{[(6-methoxy-1,2,3,4-tetrahydro-naphthalen-2-yl)-propyl-amino]-methyl}-piperidin-1-yl)-2,2-diphenyl-ethanone 66, [M+H]⁺=511;

1-(4-{[(6-methoxy-1,2,3,4-tetrahydro-naphthalen-2-yl)-propyl-amino]-methyl}-piperidin-1-yl)-ethanone 67, [M+H]⁺=359; and (1-methanesulfonyl-piperidin-4-yl)-(4-{[(6-methoxy-1,2,3,4-tetrahydro-naphthalen-2-yl)-propyl-amino]-methyl}-piperidin-1-yl)-methanone 68, [M+H]⁺=506.

Similarly following the procedure described above in Example 3, but replacing 7-methoxy-3,4-dihydro-1H-naphthalen-2-one with 6,7-dimethoxy-3,4-dihydro-1H-naphthalen-2-one in Step 1 and using the appropriate acid chlorides, sulfonyl chlorides, carbamoyl chlorides, or isocyanates in Step 4, the following compounds were prepared:

4-{[(6,7-dimethoxy-1,2,3,4-tetrahydro-naphthalen-2-yl)-propyl-amino]-methyl}-piperidine-1-carboxylic acid benzyl ester 69, [M+H]⁺=481;

(4-{[(6,7-dimethoxy-1,2,3,4-tetrahydro-naphthalen-2-yl)-propyl-amino]-methyl}-piperidin-1-yl)-furan-2-yl-methanone 70, [M+H]⁺=441;

(4-{[(6,7-dimethoxy-1,2,3,4-tetrahydro-naphthalen-2-yl)-propyl-amino]-methyl}-piperidin-1-yl)-thiophen-2-yl-methanone 71, [M+H]⁺=457;

1-(4-{[(6,7-dimethoxy-1,2,3,4-tetrahydro-naphthalen-2-yl)-propyl-amino]-methyl}-piperidin-1-yl)-2-thiophen-2-yl-ethanone 72, [M+H]⁺=471;

1-(4-{[(6,7-dimethoxy-1,2,3,4-tetrahydro-naphthalen-2-yl)-propyl-amino]-methyl}-piperidin-1-yl)-ethanone 73, [M+H]⁺=389;

(4-{[(6,7-dimethoxy-1,2,3,4-tetrahydro-naphthalen-2-yl)-propyl-amino]-methyl}-piperidin-1-yl)-(3,5-dimethyl-isoxazol-4-yl)-methanone 74, [M+H]⁺=470;

(4-{[(6,7-dimethoxy-1,2,3,4-tetrahydro-naphthalen-2-yl)-propyl-amino]-methyl}-piperidin-1-yl)-morpholin-4-yl-methanone 75, [M+H]⁺=460;

4-{[(6,7-dimethoxy-1,2,3,4-tetrahydro-naphthalen-2-yl)-propyl-amino]-methyl}-piperidine-1-carboxylic acid diethylamide 76, [M+H]⁺=446;

(4-{[(6,7-dimethoxy-1,2,3,4-tetrahydro-naphthalen-2-yl)-propyl-amino]-methyl}-piperidin-1-yl)-pyrrolidin-1-yl-methanone 77, [M+H]⁺=444;

4-{[(6,7-dimethoxy-1,2,3,4-tetrahydro-naphthalen-2-yl)-propyl-amino]-methyl}-piperidine-1-carboxylic acid dimethylamide 78, [M+H]⁺=418;

(6,7-dimethoxy-1,2,3,4-tetrahydro-naphthalen-2-yl)-(1-methanesulfonyl-piperidin-4-ylmethyl)-propyl-amine 79, [M+H]⁺=425;

4-{[(6,7-dimethoxy-1,2,3,4-tetrahydro-naphthalen-2-yl)-propyl-amino]-methyl}-piperidine-1-sulfonic acid dimethylamide 80, [M+H]⁺=454;

(6,7-dimethoxy-1,2,3,4-tetrahydro-naphthalen-2-yl)-propyl-(1-trifluoromethanesulfonyl-piperidin-4-ylmethyl)-amine 81, [M+H]⁺=479;

(6,7-dimethoxy-1,2,3,4-tetrahydro-naphthalen-2-yl)-propyl-[1-(thiophene-2-sulfonyl)-piperidin-4-ylmethyl]-amine 82, [M+H]⁺=479;

4-{[(6,7-dimethoxy-1,2,3,4-tetrahydro-naphthalen-2-yl)-propyl-amino]-methyl)-piperidine-1-carboxylic acid methylamide 83, [M+H]⁺=404; and

[1-(5-chloro-thiophene-2-sulfonyl)-piperidin-4-ylmethyl]-(6,7-dimethoxy-1,2,3,4-tetrahydro-naphthalen-2-yl)-propyl-amine 84, [M+H]⁺=527.

Example 4

N-{7-[(1-methanesulfonyl-piperidin-4-ylmethyl)-propyl-amino]-5,6,7,8-tetrahydro-naphthalen-2-yl}-isobutyramide

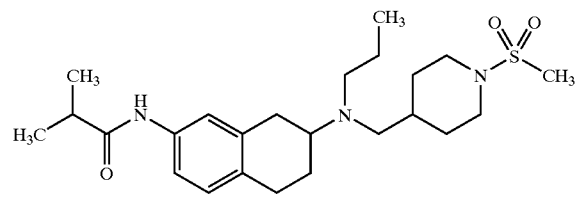

Step 1:

(7-Nitro-1,2,3,4-tetrahydro-naphthalen-2-yl)-piperidin-4-ylmethyl-propyl-amine

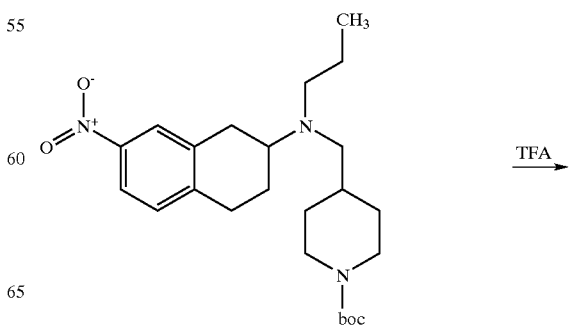

-continued

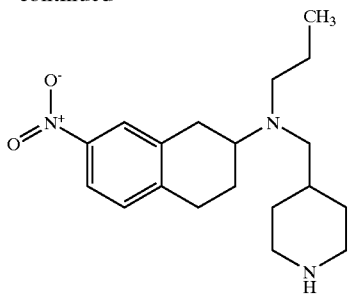

To a solution of 4-{[(7-nitro-1,2,3,4-tetrahydro-naphthalen-2-yl)-propyl-amino]-methyl}-piperidine-1-carboxylic acid tert-butyl ester, prepared as in Example 1 (1.12 g, 2.60 mmol) in methylene chloride (30 mL) under a nitrogen atmosphere was added trifluoroacetic acid (10 mL). The reaction was stirred at room temperature for 30 min. and concentrated in vacuo. The residue was partitioned between EtOAc (50 mL) and 10% aq. KOH (50 mL). The organic layer was separated, dried over MgSO$_4$, filtered, and concentrated to afford (7-nitro-1,2,3,4-tetrahydro-naphthalen-2-yl)-piperidin-4-ylmethyl-propyl-amine (845 mg).

Step 2:
(1-Methanesulfonyl-piperidin-4-ylmethyl)-(7-nitro-1,2,3,4-tetrahydro-naphthalen-2-yl)-propyl-amine

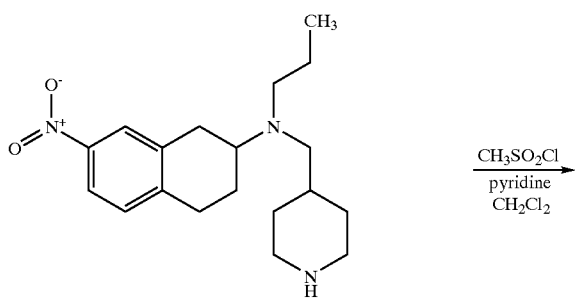

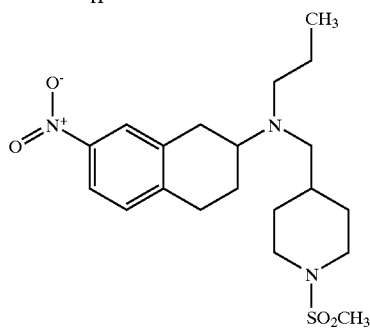

To an ice-cold solution of (7-nitro-1,2,3,4-tetrahydro-naphthalen-2-yl)-piperidin-4-ylmethyl-propyl-amine (420 mg, 1.3 mmol) and pyridine (154 μl, 1.5 mmol, 1.2 eq.) in methylene chloride (30 mL) under an inert atmosphere methanesulfonyl chloride (154 μl, 1.9 mmol, 1.5 eq) was added dropwise. The reaction was allowed to warm to room temperature and stir for 24 h. The reaction was quenched with water and the methylene chloride layer separated, dried (MgSO$_4$), and concentrated to afford (1-methanesulfonyl-piperidin-4-ylmethyl)-(7-nitro-1,2,3,4-tetrahydro-naphthalen-2-yl)-propyl-amine as a beige solid (454 mg).

Step 3:
N-(1-Methanesulfonyl-piperidin-4-ylmethyl)-N-propyl-1,2,3,4-tetrahydro-naphthalene-2,7-diamine

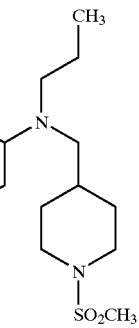

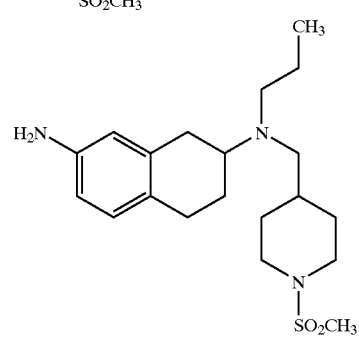

To a solution of (1-methanesulfonyl-piperidin-4-ylmethyl)-(7-nitro-1,2,3,4-tetrahydro-naphthalen-2-yl)-propyl-amine (490 mg, 1.20 mmol) in ethanol (30 mL) was added 10% palladium on charcoal (50 mg). The solution was shaken on a Parr shaker for 24 h at 55 psi of H$_2$. The solution was filtered through Celite® and concentrated to afford N-(1-methanesulfonyl-piperidin-4-ylmethyl)-N-propyl-1,2,3,4-tetrahydro-naphthalene-2,7-diamine (400 mg) 85, [M+H]$^+$=380, which was used directly in the next step.

Step 4:
N-{7-[(1-Methanesulfonyl-piperidin-4-ylmethyl)-propyl-amino]-5,6,7,8-tetrahydro-naphthalen-2-yl}-isobutyramide

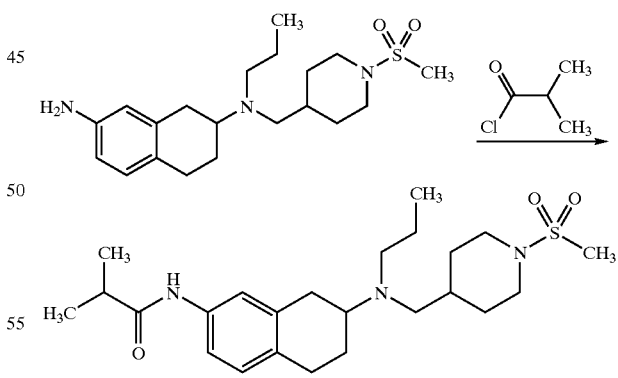

To a solution of N-(1-methanesulfonyl-piperidin-4-ylmethyl)-N-propyl-1,2,3,4-tetrahydro-naphthalene-2,7-diamine (200 μL of a 0.25 M solution in dichloromethane, 50 μmole) was added 220 μL of a 0.25 M solution of isobutyryl chloride in dichloromethane and 30 μL of DIEA. The solution was allowed to stir for 72 h at 25° C. under N$_2$ and was then concentrated in vacuo. The final product was isolated by preparative RPHPLC (YMC Combiprep ODS-A column, 10-90% acetonitrile: water (0.1% TFA)) to afford N-{7-[(1-methanesulfonyl-piperidin-4-ylmethyl)-propyl-amino]-5,6,7,8-tetrahydro-naphthalen-2-yl}-isobutyramide (10.4 mg) 86, [M+H]$^+$=450.

Similarly following the procedure described above in Example 4, Step 4, but replacing isobutyryl chloride with the appropriate acid chlorides, sulfonyl chlorides, or carboxaldehydes the following compounds have been prepared:

N-{7-[(1-methanesulfonyl-piperidin-4-ylmethyl)-propyl-amino]-5,6,7,8-tetrahydro-naphthalen-2-yl}-2,2-dimethyl-propionamide 87, [M+H]$^+$=464;

N-{7-[(1-methanesulfonyl-piperidin-4-ylmethyl)-propyl-amino]-5,6,7,8-tetrahydro-naphthalen-2-yl}-methanesulfonamide 88, [M+H]$^+$=458;

3-{7-[(1-methanesulfonyl-piperidin-4-ylmethyl)-propyl-amino]-5,6,7,8-tetrahydro-naphthalen-2-yl}-N,N-dimethylaminosulfonamide 89, [M+H]$^+$=487;

pyrrolidine-1-sulfonic acid {7-[(1-methanesulfonyl-piperidin-4-ylmethyl)-propyl-amino]-5,6,7,8-tetrahydro-naphthalen-2-yl}-amide 90, [M+H]$^+$=513;

1-{7-[(1-methanesulfonyl-piperidin-4-ylmethyl)-propyl-amino]-5,6,7,8-tetrahydro-naphthalen-2-yl}-3-methyl-urea 91, [M+H]$^+$=437;

1-isopropyl-3-{7-[(1-methanesulfonyl-piperidin-4-ylmethyl)-propyl-amino]-5,6,7,8-tetrahydro-naphthalen-2-yl}-urea 92, [M+H]$^+$=465;

1-tert-butyl-3-{7-[(1-methanesulfonyl-piperidin-4-ylmethyl)-propyl-amino]-5,6,7,8-tetrahydro-naphthalen-2-yl}-urea 93, [M+H]$^+$=479; and N$^2$-isobutyl-N$^2$-(1-methanesulfonyl-piperidin-4-ylmethyl)-N$^2$-propyl-1,2,3,4-tetrahydro-naphthalene-2,7-diamine 94 [M+H]$^+$=436.

Example 5

N-(7-{[1-(Mopholine-4-carbonyl)-piperidin-4-ylmethyl]-propyl-amino}-5,6,7,8-tetrahydro-naphthalen-2-yl)-isobutyramide

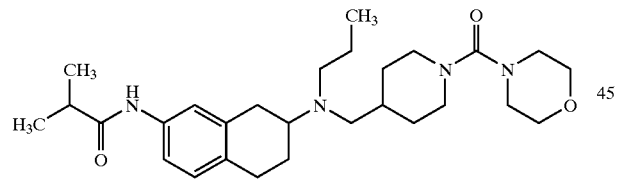

Step 1:
Morpholin-4-yl-(4-{[(7-nitro-1,2,3,4-tetrahydro-naphthalen-2-yl)-propyl-amino]-methyl}-piperidin-1-yl)-methanone

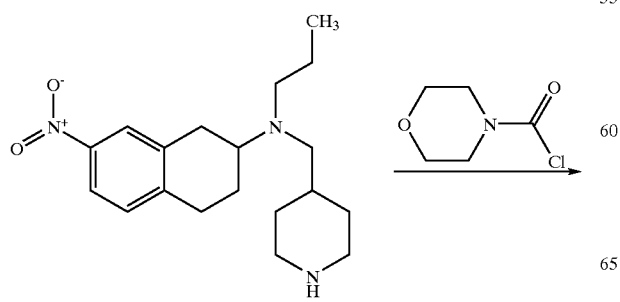

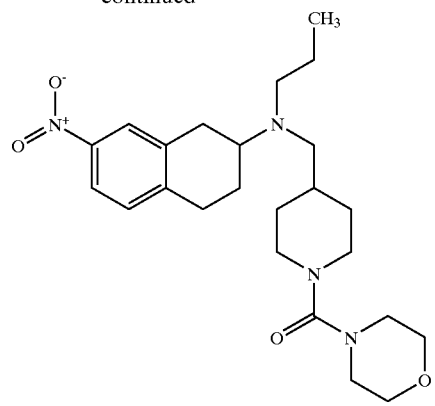

To an ice-cold solution of (7-nitro-1,2,3,4-tetrahydro-naphthalen-2-yl)-piperidin-4-ylmethyl-propyl-amine, as prepared in Example 4, (400 mg, 1.2 mmol) and triethylamine (170 μl, 1.4 mmol, 1.2 eq.) in methylene chloride (40 mL) under an inert atmosphere morpholine-4-carbonyl chloride (170 μL, 1.4 mmol) was added dropwise. The ice bath was removed and the reaction was stirred at room temperature for 4 h. The methylene chloride was washed 2 times with water (30 mL), dried (MgSO$_4$), filtered, and concentrated to afford morpholin-4-yl-(4-{[(7-nitro-1,2,3,4-tetrahydro-naphthalen-2-yl)-propyl-amino]-methyl}-piperidin-1-yl)-methanone as a clear oil (540 mg).

Step 2:
(4-{[(7-Amino-1,2,3,4-tetrahydro-naphthalen-2-yl)-propyl-amino]-methyl}-piperidin-1-yl)-morpholin-4-yl-methanone

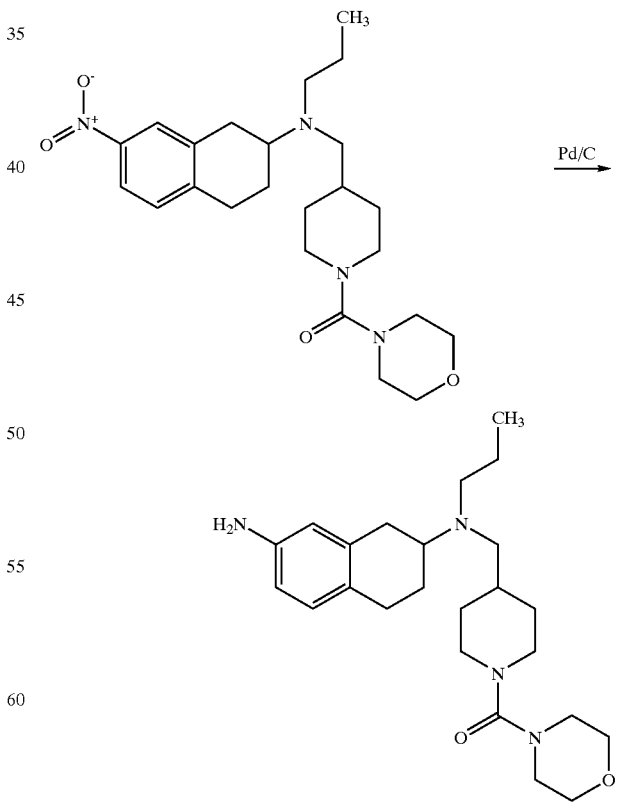

To a solution of morpholin-4-yl-(4-{[(7-nitro-1,2,3,4-tetrahydro-naphthalen-2-yl)-propyl-amino]-methyl}- piperidin-1-yl)-methanone (540 mg, 1.2 mmol) in ethanol (30 mL) was added 10% palladium on charcoal (50 mg). The solution was shaken on a Parr shaker for 24 h at 55 psi of hydrogen. The solution was filtered through Celite® and concentrated to afford (4-{[(7-amino-1,2,3,4-tetrahydro-naphthalen-2-yl)-propyl-amino]-methyl}-piperidin-1-yl)-morpholin-4-yl-methanone (432 mg) 95, [M+H]$^+$=415; which was used directly.

Step 3:
N-(7-{[1-(Morpholine-4-carbonyl)-piperidin-4-ylmethyl]-propyl-amino}-5,6,7,8-tetrahydro-naphthalen-2-yl)-isobutyramide

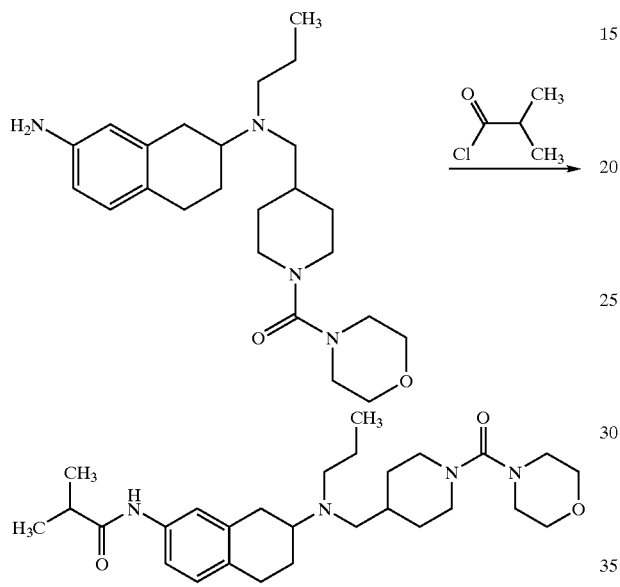

To a solution of (4-{[(7-amino-1,2,3,4-tetrahydro-naphthalen-2-yl)-propyl-amino]-methyl}-piperidin-1-yl)-morpholin-4-yl-methanone (200 μL of 0.25 M in dichloromethane, 50 μmol) was added 220 μL of a 0.25 M solution of isobutyryl chloride in dichloromethane and 30 μL of DIEA. The solution was allowed to stir for 72 h at 25° C. under N$_2$ and was then concentrated in vacuo. The final product was isolated by preparative RPHPLC (YMC Combiprep ODS-A column, 10–90% acetonitrile: water (0.1% TFA)) to afford N-(7-{[1-(morpholine-4-carbonyl)-piperidin-4-ylmethyl]-propyl-amino}-5,6,7,8-tetrahydro-naphthalen-2-yl)-isobutyramide (8.6 mg) 96, [M+H]$^+$=485.

Similarly, following the procedure described above in Example 5, step 3, but replacing isobutyryl chloride with the appropriate acid chlorides, sulfonyl chlorides, carbamoyl chlorides, or carboxaldehydes the following compounds were prepared:

2,2-dimethyl-N-(7-{[1-(morpholine-4-carbonyl)-piperidin-4-ylmethyl]-propyl-amino}-5,6,7,8-tetrahydro-naphthalen-2-yl)-propionamide 97, [M+H]$^+$=499;

N-(7-{[1-(morpholine-4-carbonyl)-piperidin-4-ylmethyl]-propyl-amino}-5,6,7,8-tetrahydro-naphthalen-2-yl)-methanesulfonamide 98, [M+H]$^+$=493;

N-(7-{[1-(morpholine-4-carbonyl)-piperidin-4-ylmethyl]-propyl-amino}-5,6,7,8-tetrahydro-naphthalen-2-yl)-N,N-dimethylaminosulfonamide 99, [M+H]$^+$=522;

pyrrolidine-1-sulfonic acid (7-{[1-(morpholine-4-carbonyl)-piperidin-4-ylmethyl]-propyl-amino)-5,6,7,8-tetrahydro-naphthalen-2-yl)-amide 100, [M+H]$^+$=548;

1-isopropyl-3-(7-{[1-(morpholine-4-carbonyl)-piperidin-4-ylmethyl]-propyl-amino}-5,6,7,8-tetrahydro-naphthalen-2-yl)-urea 101, [M+H]$^+$=500;

1-ter-butyl-3-(7-{[1-(morpholine-4-carbonyl)-piperidin-4-ylmethyl]-propyl-amino}-5,6,7,8-tetrahydro-naphthalen-2-yl)-urea 102, [M+H]$^+$=514; and (4-{[(7-isobutylamino-1,2,3,4-tetrahydro-naphthalen-2-yl)-propyl-amino]-methyl}-piperidin-1-yl)-morpholin-4-yl-methanone 103, [M+H]$^+$=471.

Example 6

(7-Ethoxy-1,2,3,4-tetrahydro-naphthalen-2-yl)-(1-methanesulfonyl-piperidin-4-ylmethyl)-propyl-amine

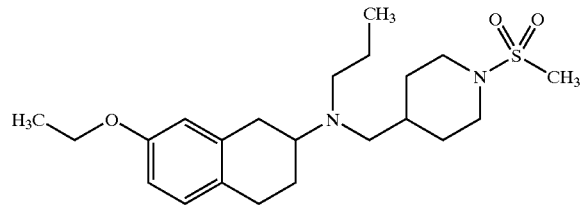

Step 1:
(7-Methoxy-1,2,3,4-tetrahydro-naphthalen-2-yl)-propyl-amine

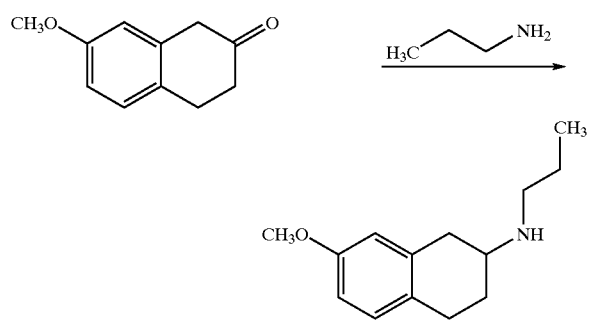

To a solution of 7-methoxy-3,4-dihydro-1H-naphthalen-2-one (6.0 g, 39.7 mmol) in dichloroethane (130 mL) under an inert atmosphere was added propylamine (3.4 mL, 41.7 mmol, 1.05 eq) followed by sodium triacetoxyborohydride (21 g, 99.3 mmol, 2.5 eq) in a single portion. The reaction was allowed to stir at room temperature for 24 h. The mixture was concentrated in vacuo and partitioned between EtOAc (200 mL) and 5% aq. NaOH (100 mL). The aqueous layer was extracted twice more with EtOAc (2×70 mL). The combined organic layers were washed with brine (100 mL), dried over MgSO$_4$, filtered, and concentrated. The residue was taken up in ether (125 mL) and treated with 1N HCl in ether. The salt was filtered and dried to afford (7-methoxy-1,2,3,4-tetrahydro-naphthalen-2-yl)-propyl-amine hydrochloride as a tan solid (5.0 g).

Step 2:
2,2,2-Trifluoro-N-(7-methoxy-1,2,3,4-tetrahydro-naphthalen-2-yl)-N-propyl-acetamide

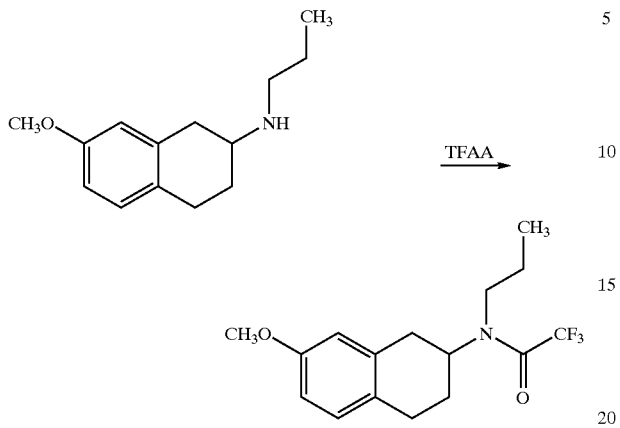

To a solution of (7-methoxy-1,2,3,4-tetrahydro-naphthalen-2-yl)-propyl-amine (3.0 g, 11.7 mmol) in dichloromethane (100 mL) under an inert atmosphere was added pyridine (2.4 mL, 29.3 mmol, 2.5 eq.). To this solution was added trifluoroacetic anhydride (1.8 mL, 12.9 mmol, 1.1 eq.) and the mixture was allowed to stir at room temperature for 24 h. The reaction was poured over 1 M HCl and the organic layer was separated and concentrated in vacuo. This was flash chromatographed on silica gel eluting with 30% acetone in hexanes to afford 2,2,2-trifluoro-N-(7-methoxy-1,2,3,4-tetrahydro-naphthalen-2-yl)-N-propyl-acetamide as an oil (3.4 g).

Step 3:
2,2,2-Trifluoro-N-(7-hydroxy-1,2,3,4-tetrahydro-naphthalen-2-yl)-N-propyl-acetamide

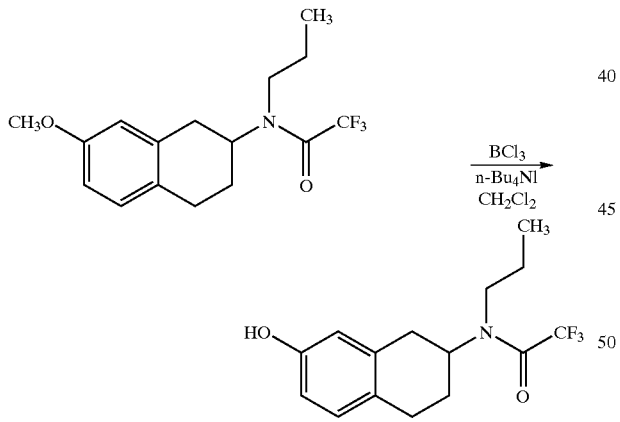

To a −78° C. solution of 2,2,2-trifluoro-N-(7-methoxy-1,2,3,4-tetrahydro-naphthalen-2-yl)-N-propyl-acetamide (3.4 g, 10.9 mmol) and tetrabutylammonium iodide (4.43 g, 12.0 mmol) in dichloromethane (200 mL) under an inert atmosphere boron trichloride (1 M, 27.2 mL) was added dropwise. The reaction was warmed to room temperature and stirred for 2.5 h. The reaction was quenched by the slow addition of water. The organic layer was separated and dried (MgSO$_4$). This was concentrated onto silica (15 g) and placed on top of a flash column. Chromatography eluting with 30% acetone in hexanes afforded 2,2,2-trifluoro-N-(7-hydroxy-1,2,3,4-tetrahydro-naphthalen-2-yl)-N-propyl-acetamide as a foam (3.1 g).

Step 4:
N-(7-Ethoxy-1,2,3,4-tetrahydro-naphthalen-2-yl)-2,2,2-trifluoro-N-propyl-acetamide

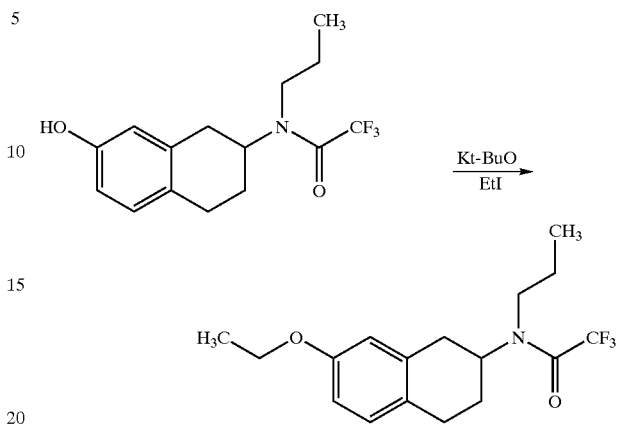

To a solution of 2,2,2-trifluoro-N-(7-hydroxy-1,2,3,4-tetrahydro-naphthalen-2-yl)-N-propyl-acetamide (1.0 g, 3.32 mmol) in DMSO (30 mL) under an inert atmosphere was added a slurry of potassium t-butoxide (392 mg, 3.49 mmol, 1.05 eq.) in DMSO (10 mL). The reaction was stirred at room temperature for 30 min. and then ethyl iodide (0.32 mL, 3.98 mmol, 1.2 eq.) was added dropwise. The reaction mixture was stirred for 2 h, quenched with water, and extracted with EtOAc (2×50 mL). The combined organic layers were dried over MgSO$_4$, filtered, and concentrated onto silica gel (10 g). This was placed on top of a flash column and eluted with 20% acetone in hexanes to afford N-(7-ethoxy-1,2,3,4-tetrahydro-naphthalen-2-yl)-2,2,2-trifluoro-N-propyl-acetamide as an oil (660 mg).

Step 5
(7-Ethoxy-1,2,3,4-tetrahydro-naphthalen-2-yl)-propyl-amine

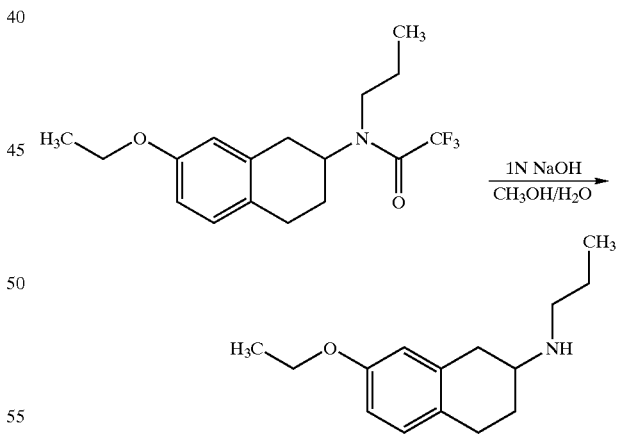

A solution of N-(7-ethoxy-1,2,3,4-tetrahydro-naphthalen-2-yl)-2,2,2-trifluoro-N-propyl-acetamide (660 mg, 2.0 mmol) in methanol (30 mL) and 1 N NaOH (30 mL) was stirred at room temperature for 30 h. The reaction was concentrated and the residue partitioned between EtOAc (40 mL) and water (40 mL). The aqueous layer was extracted twice more with EtOAc (2×30 mL). The combined organic layers were washed with brine (30 mL), dried (MgSO$_4$), and concentrated to afford (7-ethoxy-1,2,3,4-tetrahydro-naphthalen-2-yl)-propyl-amine.

Step 6:

(7-Ethoxy-1,2,3,4-tetrahydro-naphthalen-2-yl)-(1-methanesulfonyl-piperidin-4-ylmethyl)-propyl-amine

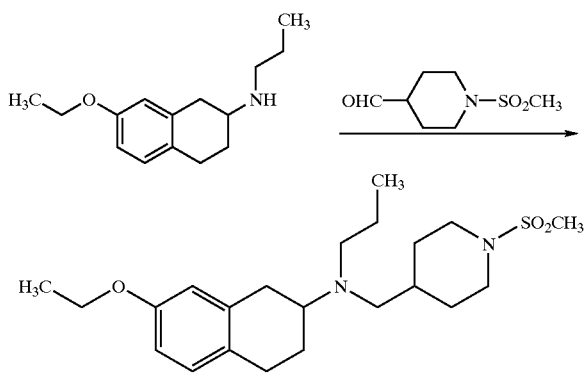

To a solution of afford (7-ethoxy-1,2,3,4-tetrahydro-naphthalen-2-yl)-propyl-amine (200 µL of a 0.25M solution in 1,2-dichloroethane, 50 µmole) was added 220 µL of a solution of 1-(methylsulfonyl)-4-piperidinecarboxaldehyde (0.25 M in 1,2-dichloroethane) followed by 30 µL DIEA and 300 µL of a 0.25 M slurry of sodium triacetoxyborohydride in 1,2-dichloroethane. The solution was shaken at 25° C. for 48 h under $N_2$. The reaction was quenched with 1 mL 2% NaOH and the mixture was transferred along with 0.5 mL $H_2O$ and EtOAc to workup flasks. The flask was shaken, allowed to settle and the aqueous phase was removed and discarded. The organic phase was washed with water, transferred into a tube and concentrated in vacuo. The final product was isolated by preparative RPHPLC (YMC Combiprep ODS-A column, 10–90% acetonitrile: water (0.1% TFA)) to afford (7-ethoxy-1,2,3,4-tetrahydro-naphthalen-2-yl)-(1-methanesulfonyl-piperidin-4-ylmethyl)-propyl-amine (8 mg) 104$[M+H]^+$=409.

Similarly following the procedure described above in Example 6, Step 1, but replacing 7-methoxy-3,4-dihydro-1H-naphthalen-2-one with 6-methoxy-3,4-dihydro-1H-naphthalen-2-one the following compound was prepared:

(6-ethoxy-1,2,3,4-tetrahydro-naphthalen-2-yl)-(1-methanesulfonyl-piperidin-4-ylmethyl)-propyl-amine 105$[M+H]^+$=409.

Example 7

Trifluoro-methanesulfonic Acid 7-{[1-(Morpholine-4-carbonyl)-piperidin-4-ylmethyl]-propyl-amino}-5,6,7,8-tetrahydro-naphthalen-2-yl Ester

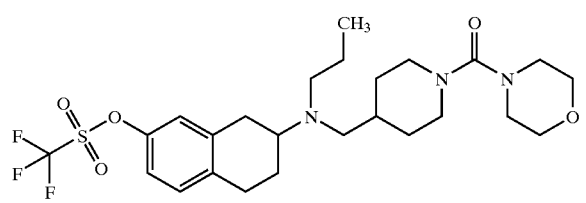

Step 1:
7-Propylamino-5,6,7,8-tetrahydro-naphthalen-2-ol

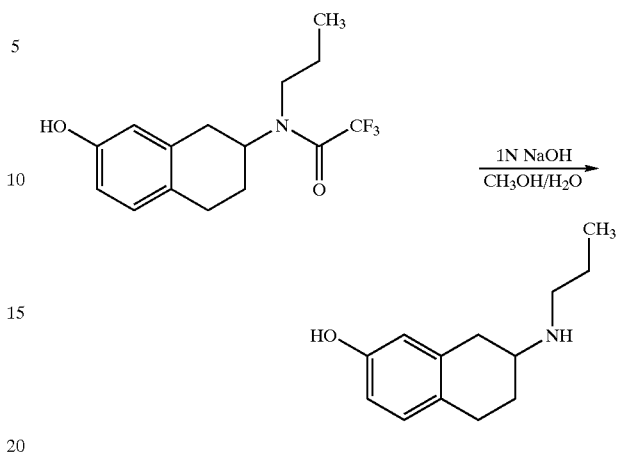

A solution of 2,2,2-trifluoro-N-(7-hydroxy-1,2,3,4-tetrahydro-naphthalen-2-yl)-N-propyl-acetamide (340 mg, 1.03 mmol) in methanol (30 mL) and 1N NaOH (30 mL) were stirred at room temperature for 30 h. The reaction was concentrated and the residue partitioned between EtOAc (40 mL) and water (40 mL). The aqueous layer was extracted twice more with EtOAc (2×30 mL). The combined organic layers were washed with brine (30 mL), dried ($MgSO_4$), and concentrated to afford 7-propylamino-5,6,7,8-tetrahydro-naphthalen-2-ol (240 mg).

Step 2:
4-}[(7-Hydroxy-1,2,3,4-tetrahydro-naphthalen-2-yl)-propyl-amino]-methyl}-piperidine-1-carboxylic Acid terl-Butyl Ester

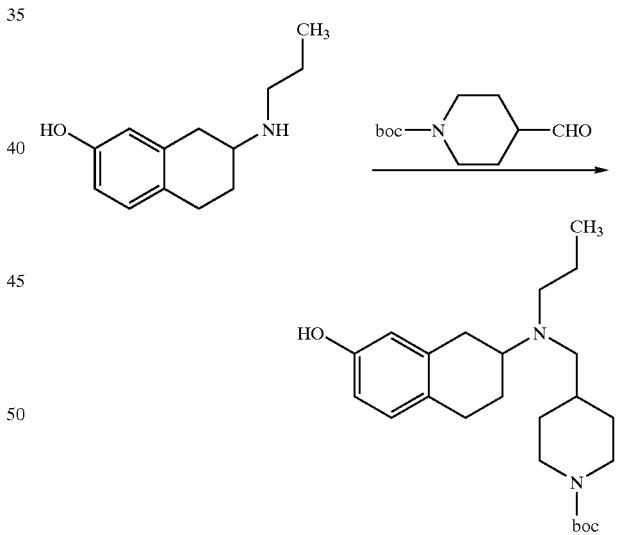

To a solution of 7-propylamino-5,6,7,8-tetrahydro-naphthalen-2-ol (937 mg, 4.6 mmol) and 4-formyl-piperidine-1-carboxylic acid tert-butyl ester (1.46 g, 6.9 mmol) in dichloroethane (40 mL) was added sodium triacetoxyborohydride (2.1 g, 10.12 mmol) in a single portion. The reaction was allowed to stir at room temperature for 24 h. The reaction was concentrated in vacuo and partitioned between EtOAc (75 mL) and 5% aq. KOH (75 mL). The organic layer was dried ($MgSO_4$), filtered, and concentrated to afford 4-{[(7-hydroxy-1,2,3,4-tetrahydro-naphthalen-2-yl)-propyl-amino]-methyl}-piperidine-1-carboxylic acid tert-butyl ester (1.37 g).

Step 3:

4-}[Propyl-(7-trifluoromethanesulfonyloxy-1,2,3,4-tetrahydro-naphthalen-2-yl)-amino]-methyl}-piperidine-1-carboxylic Acid tert-Butyl Ester

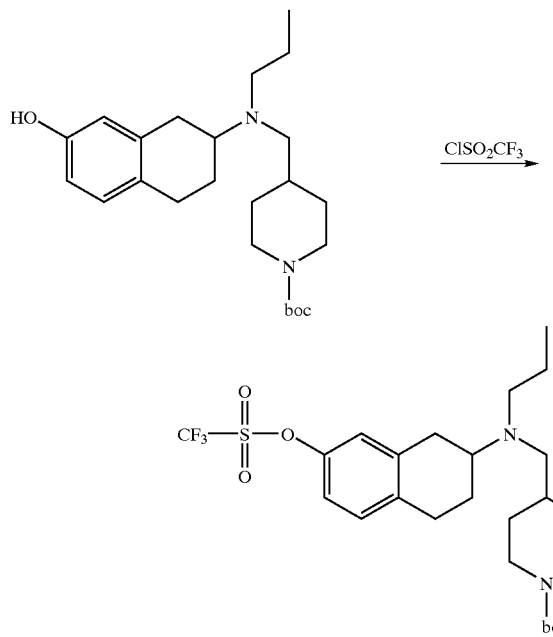

To an ice cold solution of 4-{[(7-hydroxy-1,2,3,4-tetrahydro-naphthalen-2-yl)-propyl-amino]-methyl}-piperidine-1-carboxylic acid tert-butyl ester (300 mg, 0.75 mmol) in methylene chloride (30 mL) under a nitrogen atmosphere was added triethylamine (0.16 ml, 1.125 mmol) followed by trifluoromethanesulfonyl chloride (0.08 ml, 0.78 mmol). The reaction was stirred in the ice bath for 30 min. and then added to water (60 ml). The organic layer was separated, dried over MgSO$_4$, filtered, and concentrated. Chromatography with 40% acetone in hexanes affords 4-{[propyl-(7-trifluoromethanesulfonyloxy-1,2,3,4-tetrahydro-naphthalen-2-yl)-amino]-methyl}-piperidine-1-carboxylic acid tert-butyl ester (220 mg).

Step 4:

Trifluoro-methanesulfonic Acid 7-(Piperidin-4-ylmethyl-propyl-amino)-5,6,7,8-tetrahydro-naphthalen-2-yl Ester

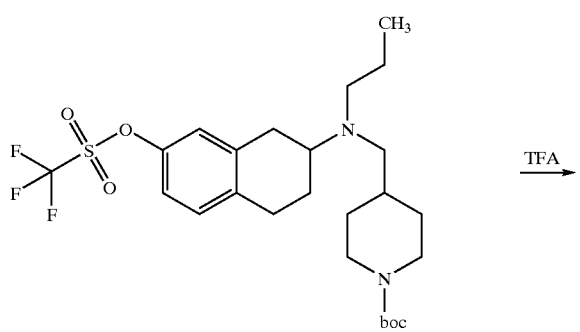

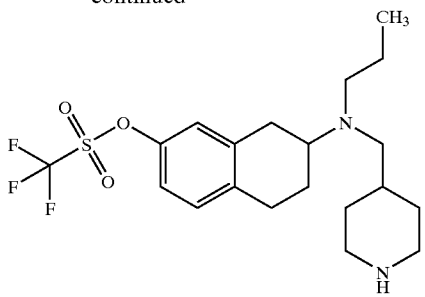

To a solution of 4-{[propyl-(7-trifluoromethanesulfonyloxy-1,2,3,4-tetrahydro-naphthalen-2-yl)-amino]-methyl}-piperidine-1-carboxylic acid tert-butyl ester, (220 mg, 0.41 mmol) in methylene chloride (5.0 mL) under an inert atmosphere was added trifluoroacetic acid (1.0 ml). The reaction was stirred at room temperature for 1h. The reaction was concentrated in-vacuo and partitioned between 1N NaOH (20 ml) and EtOAc (30 ml). The organic layer was separated, dried (MgSO$_4$), and concentrated to afford trifluoro-methanesulfonic acid 7-(piperidin-4-ylmethyl-propyl-amino)-5,6,7,8-tetrahydro-naphthalen-2-yl ester (114 mg).

Step 5:

Trifluoro-methanesulfonic Acid 7-{[1-(Morpholine-4-carbonyl)-piperidin-4-ylmethyl]-propyl-amino}-5,6,7,8-tetrahydro-naphthalen-2-yl Ester

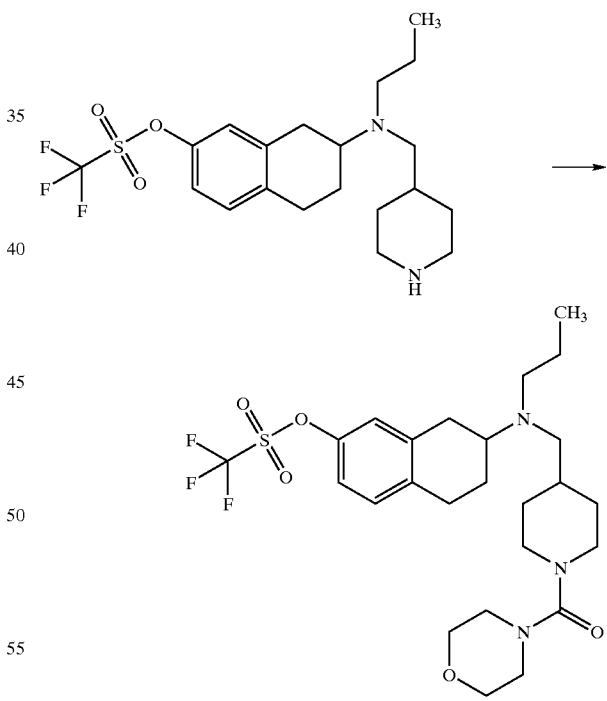

To a solution of trifluoro-methanesulfonic acid 7-(piperidin-4-ylmethyl-propyl-amino)-5,6,7,8-tetrahydro-naphthalen-2-yl ester (200 μL of a 0.19 M solution in acetonitrile, 36 μmole) was added 220 μL of a 0.25 M solution of morpholine 4-carbonyl chloride in dichloromethane and 30 μL of DIEA. The solution was allowed to stir for 48 h at 25° C. under N$_2$, and was then concentrated in vacuo. The final product was isolated by preparative RPHPLC (YMC Combiprep ODS-A column, 10–90% acetonitrile: water (0.1% TFA)) to afford trifluoro-methanesulfonic acid 7-{[1-(morpholine-4-carbonyl)-piperidin-4-ylmethyl]-propyl-amino}-5,6,7,8-tetrahydro-naphthalen-2-yl ester (12.8 mg) 106[M+H]$^+$=548.

Similarly, following the procedure described above in Example 7, step 5, but replacing morpholine 4-carbonyl chloride with the appropriate acid chloride, carbamoyl chloride, or sulfonyl chloride the following compounds were prepared:

trifluoro-methanesulfonic acid 7-{[1-(isoxazole-5-carbonyl)-piperidin-4-ylmethyl]-propyl-amino}-5,6,7,8-tetrahydro-naphthalen-2-yl ester 107[M+H]$^+$=530;

trifluoro-methanesulfonic acid 7-[(1-dimethylcarbamoyl-piperidin-4-ylmethyl)-propyl-amino]-5,6,7,8-tetrahydro-naphthalen-2-yl ester 108[M+H]$^+$=506;

trifluoro-methanesulfonic acid 7-[(1-methanesulfonyl-piperidin-4-ylmethyl)-propyl-amino]-5,6,7,8-tetrahydro-naphthalen-2-yl ester 109[M+H]$^+$=513; and trifluoro-methanesulfonic acid 7-{[1-(1-methyl-1H-imidazole-4-sulfonyl)-piperidin-4-ylmethyl]-propyl-amino}-5,6,7,8-tetrahydro-naphthalen-2-yl ester 111O [M+H]$^+$=579.

Example 8

[7-(3-Amino-phenyl)-1,2,3,4-tetrahydro-naphthalen-2-yl]-(1-methanesulfonyl-piperidin-4-ylmethyl)-propyl-amine

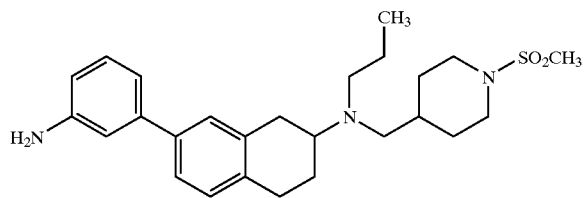

Step 1:
(7-Bromo-1,2,3,4-tetrahydro-naphthalen-2-yl)-propyl-amine

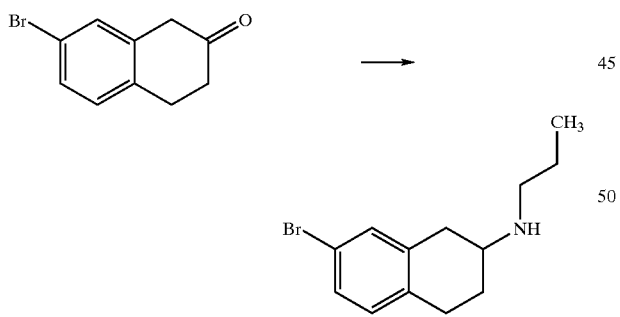

To a solution of 7-bromo-3,4-dihydro-1H-naphthalen-2-one, prepared as described in J. Med. Chem, 1993, 36, 2279–2291, (5.2 g, 23 mmol) in 1,2 dichloroethane (30 mL), propyl amine (1.63 g, 28 mmol) was added, followed by addition of sodium triacetoxyborohydride (7.3 g, 34.5 mmol). The reaction was stirred at ambient temperature under nitrogen for 24 h, at which time it was concentrated in vacuo. The remaining solid was partitioned between 1 M sodium hydroxide and ethyl acetate. The ethyl acetate was washed with brine, dried over magnesium sulfate, and filtered to yield (7-bromo-1,2,3,4-tetrahydro-naphthalen-2-yl)-propyl-amine (2.75 g).

Step 2:
(7-Bromo-1,2,3,4-tetrahydro-naphthalen-2-yl)-(1-methanesulfonyl-piperidin-4-ylmethyl)-propyl-amine

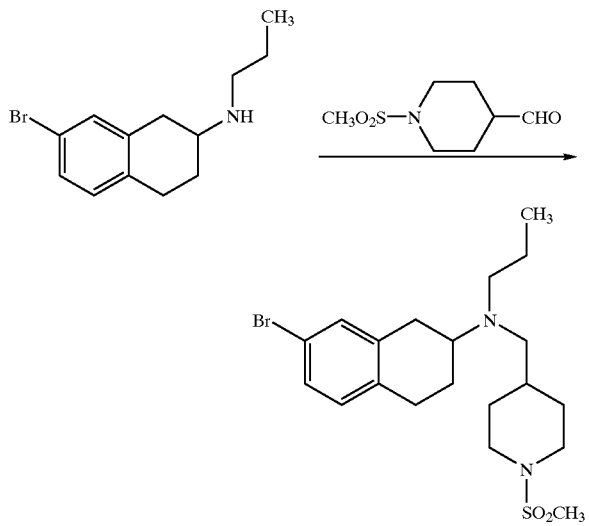

To a solution of (7-bromo-1,2,3,4-tetrahydro-naphthalen-2-yl)-propyl-amine (536 mg, 2 mmol) and 1-methanesulfonyl-piperidine-4-carboxaldehyde (458 mg, 2.47 mmol) in dichloroethane (10 mL) was added sodium triacetoxyborohydride (551 mg, 2.6 mmol) in a single portion. The reaction was stirred at room temperature for 24 h. The reaction was concentrated in vacuo and partitioned between EtOAc (75 mL) and 5% aq. KOH (75 mL). The organic layer was dried (MgSO$_4$), filtered, and concentrated to afford (7-bromo-1,2,3,4-tetrahydro-naphthalen-2-yl)-(1-methanesulfonyl-piperidin-4-ylmethyl)-propyl-amine (857 mg) 111 [M+H]$^+$=444.

Step 3:
[7-(3-Amino-phenyl)-1,2,3,4-tetrahydro-naphthalen-2-yl-(1-methanesulfonyl-piperidin-4-ylmethyl)-propyl-amine

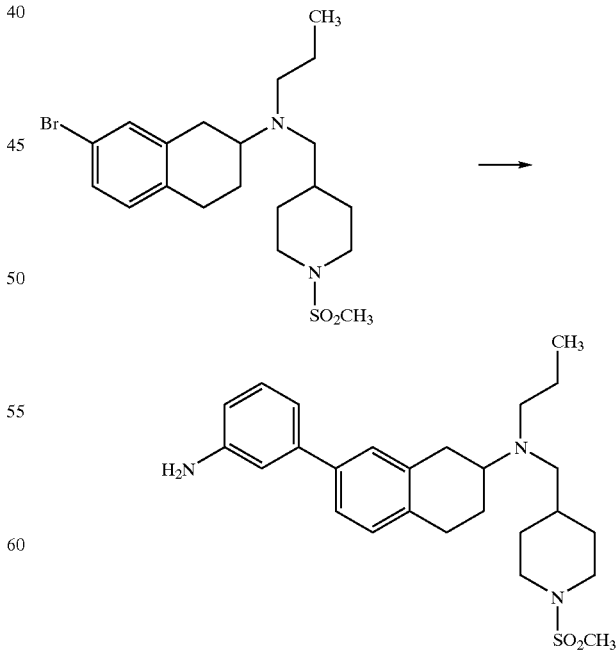

A 1 mL solution of (7-bromo-1,2,3,4-tetrahydro-naphthalen-2-yl)-(1-methanesulfonyl-piperidin-4- ylmethyl)-propyl-amine (25 mmole in DMA) was added to a tube containing 2–3 mg Pd(PPh$_3$)$_4$ catalyst followed by 120 µL of a solution of 3-amino phenyl boronic acid (30 mmole in DMA), and 200 µL 1N aq. NaOH. The solution was shaken at 80° C. for 4 h, concentrated, and purified by chromatography to yield [7-(3-amino-phenyl)-1,2,3,4-tetrahydro-naphthalen-2-yl]-(1-methanesulfonyl-piperidin-4-ylmethyl)-propyl-amine 112[M+H]$^+$=456.

Similarly, following the procedure described above in Example 8, step 3, but replacing 3-aminophenyl boronic acid with the appropriate boronic acid derivatives the following compound was prepared:

[7-(4-methanesulfonyl-phenyl)-1,2,3,4-tetrahydro-naphthalen-2-yl]-(1-methanesulfonyl-piperidin-4-ylmethyl)-propyl-amine 113[M+H]$^+$=519;

(7-furan-2-yl-1,2,3,4-tetrahydro-naphthalen-2-yl)-(1-methanesulfonyl-piperidin-4-ylmethyl)-propyl-amine 117[M+H]$^+$=431;

(7-furan-3-yl-1,2,3,4-tetrahydro-naphthalen-2-yl)-(1-methanesulfonyl-piperidin-4-ylmethyl)-propyl-amine 118[M+H]$^+$=431;

(1-methanesulfonyl-piperidin-4-ylmethyl)-propyl-(7-pyridin-3-yl-1,2,3,4-tetrahydro-naphthalen-2-yl)-amine 119[M+H]$^+$=442;

(1-methanesulfonyl-piperidin-4-ylmethyl)-propyl-[7-(1H-pyrrol-2-yl)-1,2,3,4-tetrahydro-naphthalen-2-yl]-amine 120[M+H]$^+$=430; and (1-methanesulfonyl-piperidin-4-ylmethyl)-propyl-(7-pyridin-4-yl-1,2,3,4-tetrahydro-naphthalen-2-yl)-amine 120[M+H]$^+$=420.

Example 9

3,5-Dimethyl-isoxazole-4-sulfonic Acid 7-{[1-(Piperidine-4-carbonyl)-piperidin-4-ylmethyl]-propyl-amino}-5,6,7,8-tetrahydro-naphthalen-2-yl Ester

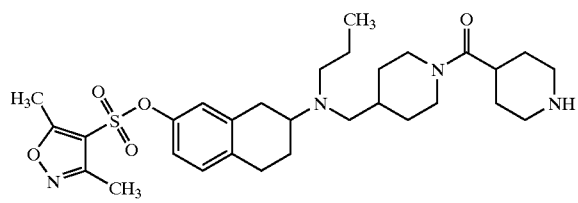

Step 1:

4-({[7-(3,5-Dimethyl-isoxazole-4-sulfonyloxy)-1,2,3,4-tetrahydro-naphthalen-2-yl]-propyl-amino}-methyl)-piperidine-1-carboxylic Acid tert-Butyl Ester

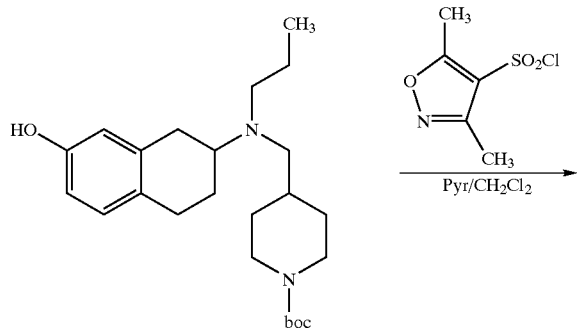

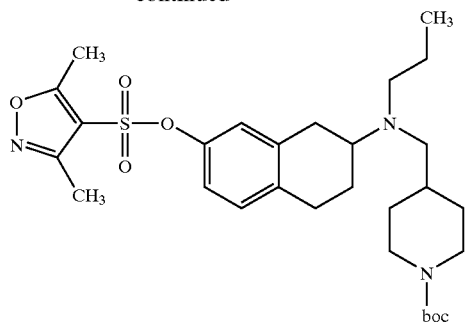

To an ice-cold solution of 4-{[(7-hydroxy-1,2,3,4-tetrahydro-naphthalen-2-yl)-propyl-amino]-methyl}-piperidine-1-carboxylic acid tert-butyl ester, prepared as described in Example 8, (1.0 g, 2.48 mmol) and triethylamine (0.52 mL, 2.73 mmol) in methylene chloride (75 mL) under an inert atmosphere 3,5-dimethyl-isoxazole-4-sulfonyl chloride (535 mg, 2.73 mmol) was added dropwise. The reaction was allowed to warm to room temperature and stirred for 24 h. The reaction was quenched with water and the methylene chloride layer was separated, dried (MgSO$_4$), and concentrated to afford 4-({[7-(3,5-dimethyl-isoxazole-4-sulfonyloxy)-1,2,3,4-tetrahydro-naphthalen-2-yl]-propyl-amino}-methyl)-piperidine-1-carboxylic acid tert-butyl ester (1.16 g).

Step 2:

3,5-Dimethyl-isoxazole-4-sulfonic Acid 7-(Piperidin-4-ylmethyl-propyl-amino)-5,6,7,8-tetrahydro-naphthalen-2-yl Ester

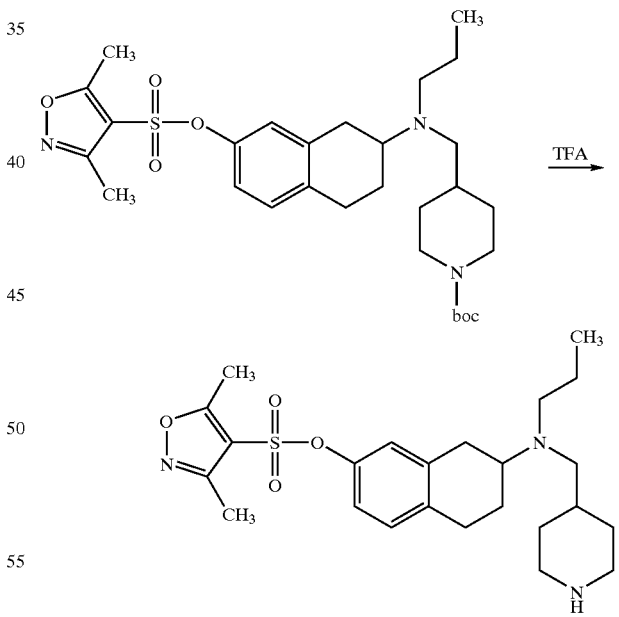

To a solution of 4-({[7-(3,5-dimethyl-isoxazole-4-sulfonyloxy)-1,2,3,4-tetrahydro-naphthalen-2-yl]-propyl-amino}-methyl)-piperidine-1-carboxylic acid tert-butyl ester (1.16 g, 2.1 mmol) in methylene chloride (30 mL) under a nitrogen atmosphere was added trifluoroacetic acid (10 mL). The reaction was stirred at room temperature for 30 min. and concentrated in vacuo. The residue was partitioned between EtOAc (50 mL) and 10% aq. KOH (50 mL). The organic layer was separated, dried over MgSO$_4$, filtered, and concentrated to afford 3,5-dimethyl-isoxazole-4-sulfonic acid 7-(piperidin-4-ylmethyl-propyl-amino)-5,6,7,8-tetrahydro-naphthalen-2-yl ester (847 mg).

Step 3:
3,5-Dimethyl-isoxazole-4-sulfonic Acid 7-{[1-(piperidine-4-carbonyl)-piperidin-4-ylmethyl]-propyl-amino}-5,6,7,8-tetrahydro-naphthalen-2-yl Ester

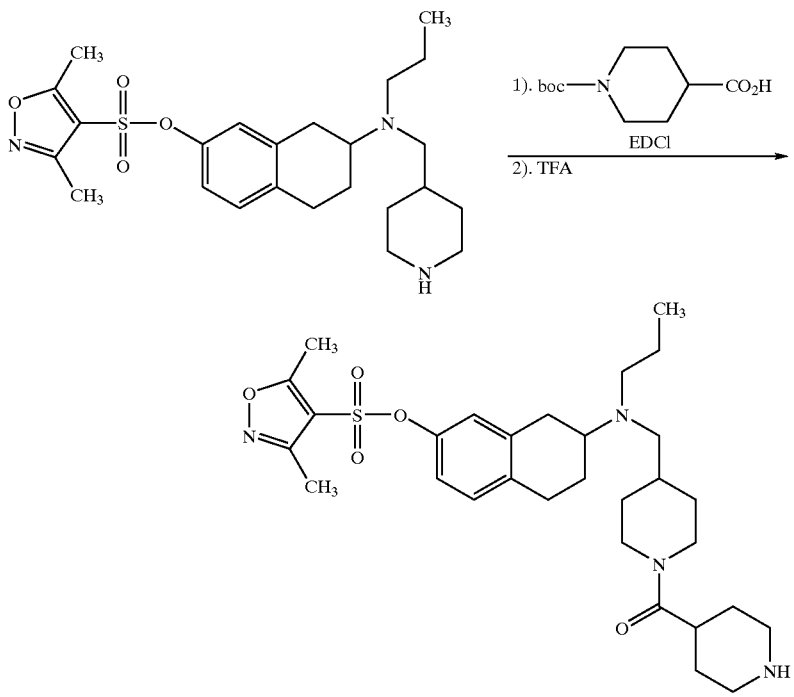

Under an inert atmosphere 3,5-dimethyl-isoxazole-4-sulfonic acid 7-(piperidin-4-ylmethyl-propyl-amino)-5,6,7,8-tetrahydro-naphthalen-2-yl ester (400 mg, 0.87 mmol), piperidine-1,4-dicarboxylic acid mono-tert-butyl ester (199 mg, 0.87 mmol, 1 eq.), EDCl (166 mg, 0.87 mmol, 1 eq.), triethylamine (0.25 mL, 1.79 mmol, 2 eq.), and dichloromethane (35 mL) were combined. The mixture was stirred at room temperature for 48 h and then concentrated in vacuo. The residue was taken up in EtOAc (50 mL) and washed with water (30 mL), 1 N NaOH (30 mL), brine (30 mL), and then dried (MgSO$_4$). The solution was filtered and concentrated to afford a yellow oil. The oil was flash chromatographed on silica gel eluting with 20% acetone in hexanes to afford the protected amine as a foam (447 mg), which was deprotected with trifluoroacetic acid, as described herein, to afford 3,5-dimethyl-isoxazole-4-sulfonic acid 7-{[1-(piperidine-4-carbonyl)-piperidin-4-ylmethyl]-propyl-amino}-5,6,7,8-tetrahydro-naphthalen-2-yl ester (320 mg), 114M+H]$^+$=609.

Alternatively, acylation of 3,5-dimethyl-isoxazole-4-sulfonic acid 7-(piperidin-4-ylmethyl-propyl-amino)-5,6,7,8-tetrahydro-naphthalen-2-yl ester, prepared as described above in Step 2, with 1-methyl-piperidine-4-carbonyl chloride under conditions as described herein, in Example 5, afforded 3,5-dimethyl-isoxazole-4-sulfonic acid 7-{[1-(4-methyl-piperazine-1-carbonyl)-piperidin-4-ylmethyl]-propyl-amino}-5,6,7,8-tetrahydro-naphthalen-2-yl ester 115 [M+H]$^+$=624.

Example 10

(4-{2-[((R)-7-Methoxy-1,2,3,4-tetrahydro-naphthalen-2-yl)-propyl-amino]-ethyl}-piperidin-1-yl)-piperidin-4-yl-methanone

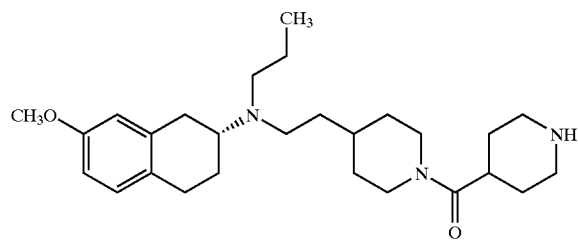

Step 1:
((R)-7-Methoxy-1,2,3,4-tetrahydro-naphthalen-2-yl)-(2-piperidin-4-yl-ethyl)-propyl-amine

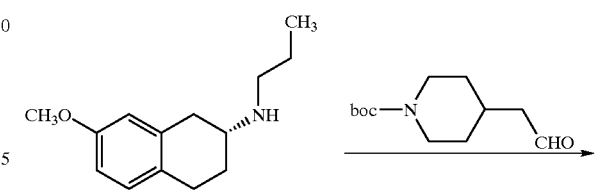

-continued

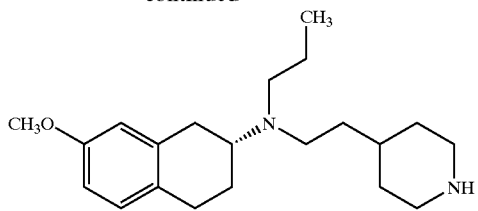

To a solution of (R)-(7-methoxy-1,2,3,4-tetrahydro-naphthalen-2-yl)-propyl-amine (510 mg, 2.0 mmol) and 4-(2-oxo-ethyl)-piperidine-1-carboxylic acid tert-butyl ester (500 mg, 2.2 mmol) in dichloroethane (40 mL) was added triethylamine (0.3 mL, 2.2mmol) and sodium triacetoxyborohydride (1.0 g, 4.75 mmol). The reaction was stirred at room temperature for 24 h. The reaction was concentrated in vacuo and partitioned between EtOAc (75 mL) and 5% aq. KOH (75 mL). The organic layer was dried (MgSO$_4$), filtered, and concentrated to afford an oil (716 mg). Deprotection with 10 mL trifluoroacetic acid, as described herein, afforded ((R)-7-methoxy-1,2,3,4-tetrahydro-naphthalen-2-yl)-(2-piperidin-4-yl-ethyl)-propyl-amine.

Step 2:

(4-{2-[(R)-7-Methoxy-1,2.3,4-tetrahydro-naphthalen-2-yl)-propyl-amino]-ethyl}-piperidin-1-yl)-piperidin-4-yl-methanone

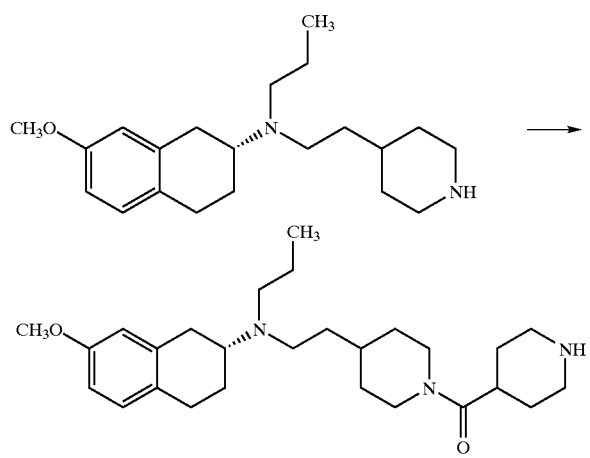

Under an inert atmosphere ((R)-7-methoxy-1,2,3,4-tetrahydro-naphthalen-2-yl)-(2-piperidin-4-yl-ethyl)-propyl-amine (200 mg, 0.61 mmol), piperidine-1,4-dicarboxylic acid mono-tert-butyl ester (139 mg, 0.61 mmol), EDCl (117 mg, 0.61 mmol), HOBT (82 mg, 0.61 mmol), triethylamine (0.17 mL, 1.2 mmol), and dichloromethane (35 mL) were combined. The mixture was stirred at room temperature for 48 h and then concentrated in-vacuo. The residue was taken-up in EtOAc (50 mL) and washed with water (30 mL), 1 N NaOH (30 mL), brine (30 mL), and dried (MgSO$_4$). The solution was filtered and concentrated to afford an oil. The oil was flash chromatographed on silica gel eluting with 20% acetone in hexanes to afford the protected amine (260 mg) which was deprotected with 10 mL trifluoroacetic acid, as described herein, to afford (4-{2-[((R)-7-methoxy-1,2,3,4-tetrahydro-naphthalen-2-yl)-propyl-amino]-ethyl}-piperidin-1-yl)-piperidin-4-yl-methanone (200 mg) 116[M+H]$^+$=478.

Example 11

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 12

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 13

Composition for Oral Administration

| Ingredient | Amount |
|---|---|
| Active compound | 1.0 g |
| Fumaric acid | 0.5 g |
| Sodium chloride | 2.0 g |
| Ingredient | Amount |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

Example 14

Parenteral Formulation (IV)

| Ingredient | % wt./wt. |
|---|---|
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter, and packaged under sterile conditions.

Example 15

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath and poured into molds containing 2.5 g total weight.

Example 16

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water, at about 60° C., is then added with vigorous stirring to emulsify the ingredients, and water is then added q.s. about 100 g.

Example 17

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust the pH. The nasal spray formulations may be delivered via a nasal spray metered pump, typically delivering about 50–100 microliters of formulation per actuation. A typical dosing schedule is 2–4 sprays every 4–12 hours.

Example 18

Radioligand Binding Studies

The inhibitory activity of compounds of this invention in vitro was determined using a modification of the method described in Hegde, S. S. et al. (1997) *Br. J. Pharmacol.*, 120, 1409–1418.

Cell membranes from Chinese hamster ovary cells expressing the recombinant human muscarinic receptors ($m_1$–$m_5$) were employed. The assays were conducted with the radioligand [$^3$H]N-methyl scopolamine(0.4 nM, specific activity 84 Ci·mmol$^{-1}$) in a final volume of 0.25 mL Tris-Krebs buffer. Non-specific binding was defined with 1 $\mu$M atropine. Assays were performed using scintillation proximity assay technology. Competition-displacement curves were generated using 10 concentrations of test compounds and were analyzed by iterative curve fitting to a four parameter logistic equation. $pIC_{50}$ values (–log of the $IC_{50}$) were converted to pKi values using the Cheng-Prusoff equation.

Compounds of this invention were active in this assay. Representative values for the M2 and M3 receptor are shown below.

| Structure | Cpd # | Ex | m2/ | m3 |
|---|---|---|---|---|
| 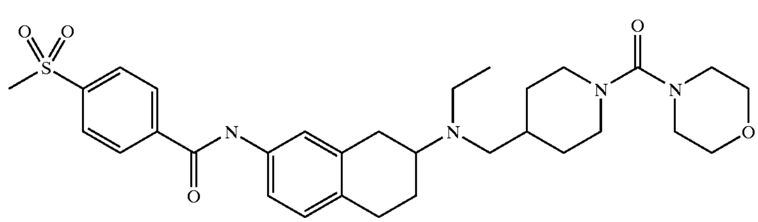 | 2 | 1 | 7.32 | 5.92 |
| 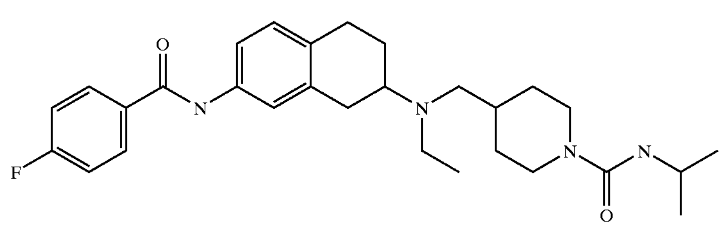 | 7 | 2 | 7.98 | 6.19 |

-continued

| Structure | Cpd # | Ex | m2/ | m3 |
|---|---|---|---|---|
| 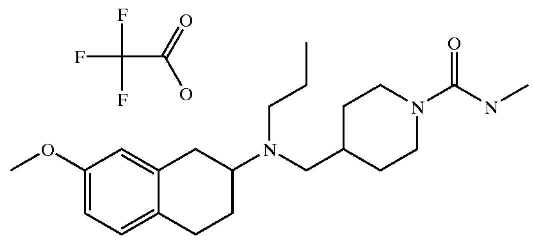 | 25 | 3 | 7.60 | 6.99 |
| 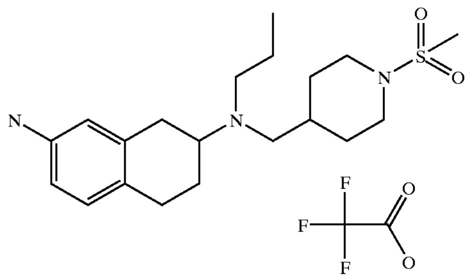 | 85 | 4 | 7.89 | 6.78 |
| 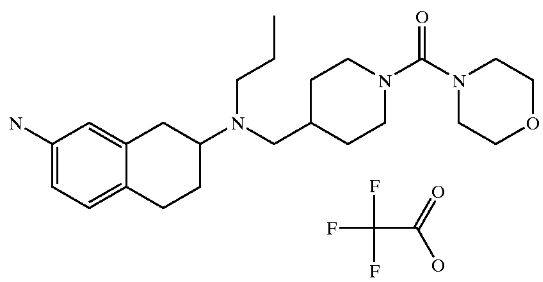 | 95 | 5 | 8.28 | 6.73 |
| 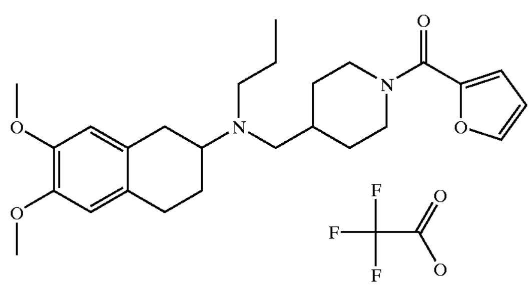 | 70 | 3 | 7.37 | 6.48 |
| 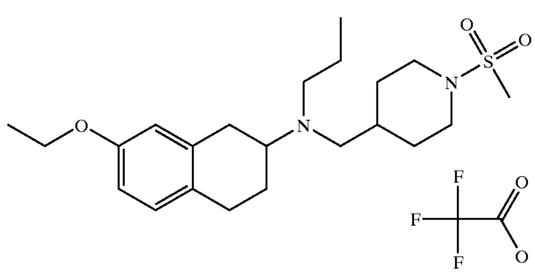 | 104 | 6 | 7.79 | 7.33 |

-continued

| Structure | Cpd # | Ex | m2/ | m3 |
|---|---|---|---|---|
| (structure) | 107 | 7 | 7.79 | 6.83 |
| (structure) | 117 | 8 | 6.85 | 6.22 |
| (structure) | 116 | 10 | 8.60 | 8.29 |
| (structure) | 114 | 9 | 8.9 | 7.29 |
| (structure) | 115 | 9 | 7.66 | 7.17 |

Example 19

Oxotremorine/Pilocarpine-Induced Salivation (OIS/PIS) Model in Anesthetized Rats Female Sprague-Dawley rats (Charles-River, 200–300 g) rats were anesthetized with urethane (1.5 g/kg, sc) and were tracheotomized. One femoral vein was cannulated for drug administration. After a one hour stabilization period, rats were pre-treated with methoctramine (only for OIS) to antagonize $M_2$ receptor mediated bradycardia. Each animal was dosed, intravenously, with a single dose of the vehicle or the reference compound. Ten minutes later, pre-weighed cotton pads were placed in the animals mouth following which they were dosed with vehicle or oxotremorine (0.1 mg/kg, iv)/pilocarpine (1 mg/kg, iv). Fresh cotton pads were placed at 5 minutes post-oxotremorine/pilocarpine and saliva collected for an additional 5 minutes. The cotton pads (5 and 10-minute period) were then re-weighed to determine the amount of saliva secreted during the 10-minute period.

All oxotremorine/pilocarpine treated groups were compared using one-way analysis of variance. Pair-wise comparisons were made using Dunnett's test. The ranked data (non-parametric technique) or actual levels of the data (parametric technique) were applied in the analysis depending upon the results of the Bartlett's test, which tests homogeneity of variances. The vehicle/oxotremorine group and vehicle/pilocarpine group were compared to the vehicle/vehicle group using Wilcox on rank-sum test. An estimate of the $ID_{50}$ for each compound with respect to the 10 minute overall secretion weight for each animal was obtained. The sigmoidal model is in the form of $$Resp = min + (max - min)/(1 + (dose/ID_{50})^{**}N)$$

where $ID_{50}$ is the dose to achieve half the maximal response, N is the curvature parameter and max is the max response for the dose response curve. The minimum response was fixed at 0 in the model.

Compounds of this invention were active in this assay.

Example 20

Inhibition of Volume-Induced Contractions in Rats

The muscarinic receptor inhibitory activity of compounds of this invention was determined in rats using a modification of the method described in Hegde, S. S. et al.(1996) *Proceedings of the 26th Annual Meeting of the International Continence Society* (August 27th–30th), Abstract 126.

Female Sprague-Dawley rats were anesthetized with urethane and instrumented for intravenous administration of drugs and, in some cases, measurement of arterial pressure, heart rate and intra-bladder pressure. The effect of test compounds on volume-induced bladder contractions was determined in separate groups of animals. Volume-induced reflex bladder contractions were induced by filling the bladder with saline. The test compounds were administered intravenously in a cumulative manner at 10-minute intervals. Atropine (0.3 mg/kg, iv) was administered at the end of the study as a positive control.

Compounds of this invention were active in this assay.

Example 21

Anti-muscarinic Activity in Anesthetized Dogs

The muscarinic receptor inhibitory activity of compounds of this invention was determined in dogs using a modification of the method described in Newgreen, D. T. et al.(1996) *J. Urol.*, 155(Suppl. 5), 1156.

Female beagles (Marshall Farms, North Rose, N.Y.) were fasted for 18 hours prior to the experiment; water was allowed ad libitum. On the day of the experiment, dogs were anesthetized and maintained on pentobarbital (36 mg/kg, iv initially, then 5–10 mg/kg, iv for maintenance). Intravenous fluids were also administered to the dogs for the remainder of the experiment. The dogs were artificially ventilated, via an endotracheal tube, with an Harvard respirator (Model 613). Both femoral veins and one femoral artery was cannulated for drug administration and blood pressure measurement, respectively. Blood pressure was measured with a Gould transducer (Model P23XL) and recorded on a Gould recorder (Model 3400). A sublingual incision was made to expose the left mandibular duct, which was then cannulated for the collection of saliva into pre-weighed vials. The left salivary gland was exposed via a submandibular incision. The chorda-lingual nerve was isolated and had a bipolar electrode placed on it for stimulation. Test responses to chorda-lingual nerve stimulation were obtained to confirm proper electrode placement.

After completion of surgery, physostigmine (180 μg/kg/hr, iv) (a cholinesterase inhibitor) was infused for the remainder of the experiment. Following a one hour stabilization period, two control chorda-lingual nerve stimulations were performed at 12 Hz, 10 V, 0.5 ms duration (Grass S48). The chorda-lingual nerve was stimulated for 20 seconds and 2 minutes, respectively, with a minimum of 10 minute interval between each set of stimulations. After two consistent control responses were obtained, the vehicle or the reference compound was dosed in a cumulative fashion, 3 minutes prior to each stimulation of the chorda-lingual nerve. Experiments in which consistent salivation responses could not be obtained were not included in the analysis. Atropine (1.0 mg/kg, iv) was given as a positive control at the end of the study.

Mean arterial blood pressure was calculated as Diastolic arterial pressure+(Systolic arterial pressure−Diastolic arterial pressure)/3. Heart rate was derived from the pressure pulse. Saliva was collected in pre-weighed vials and weighed after each collection to determine the volume of saliva secreted. Inhibition of salivary gland responses were expressed as a percent of the effect of atropine (1 mg/kg, iv).
ED50 Estimation.

For % max inhibition salivation, parameter estimation was performed using a nonlinear mixed model. The method was implemented using PROC NLIN initially and PROC MIXED iteratively. This procedure assumed the following sigmoidal dose-response model:

$$Response = Min + \frac{Max - Min}{1 + 10^{\frac{(x-\mu)}{\sigma}}}$$

where response=% max inhibition bladder contraction at peak, x=$\log_{10}$ dose of treatment and the 4 parameters were: $\log_{10}$ ED50 (μ), maximum and minimum response (Max and Min), and curvature (σ). The minimum was assumed 0%. This method assumed compound symmetry for the covariance structure. It was an iterative curve-fitting procedure that accounted for the dependence between multiple measurements from the same animal, and estimated the desired parameters and their confidence limits by adjusting its error calculations to account for within subject correlation.
Baseline Comparisons To compare each dose to baseline control for every variable, a two-way ANOVA with main effects of subject and treatment was performed, followed by a pair t-test at each dose level. If the overall treatment effect was not significant (p-value >0.05) in ANOVA, a Bonferroni adjustment for p-values was used for the p-value of pair t-test at each dose.

Compounds of this invention were active in this assay.

Example 22

In vivo Antimuscarinic Activity in Bronchoconstriction Assays

Antagonist activity is assessed against methacholine-induced bronchoconstriction and bradycardia in the anesthetized rat model following a procedure similar to that described by Hirose et al, 2001, *J. Pharm. Exp. Ther.*, Vol 297, 790–797. Compounds are given intravenously, orally or by intratracheal instillation prior to challenge with intravenous methacholine. Lung resistance and dynamic compliance are used as indices of bronchoconstriction.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound comprising Formula I

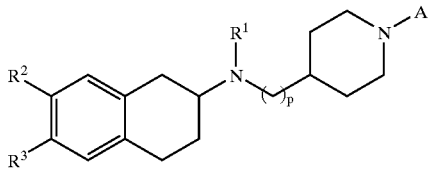

Formula I wherein:

A is —C(O)R$^4$ or —S(O)$_2$R$^5$;

R$^1$ is (C$_{1-6}$)alkyl or allyl;

R$^2$ and R$^3$ are independently in each occurrence hydrogen, halogen, (C$_{1-6}$)alkyl, haloalkyl, —OR', —S(O)$_{0-2}$R', —NR'R", —NR'COR", —NR'''CONR'R", —NR'SO$_2$R", —NR'''SO$_2$NR'R", —SO$_2$NR'R", —OSO$_2$R', nitro, cyano, heteroaryl, or aryl, wherein said heteroaryl or aryl group is optionally substituted with one or more groups selected from hydroxy, cyano, (C$_{1-6}$)alkyl, (C$_{1-6}$)alkoxy, haloalkoxy, alkylthio, halo, haloalkyl, hydroxyalkyl, nitro, alkoxycarbonyl, amino, alkylamino, alkylsulfonyl, alkylcarbonyl, alkylaminosulfonyl, alkylsulfonylamino, alkylaminocarbonyl, and alkylcarbonylamino, with the proviso that R$^2$ and R$^3$ are not both hydrogen;

with the proviso that R$^2$ and R$^3$ are not both hydrogen;

R', R", and R''' are independently in each occurrence hydrogen, (C$_{1-6}$)alkyl, (C$_{3-6}$)cycloalkyl, haloalkyl, diphenylmethyl, aryl or aryl(C$_{1-6}$)alkyl, wherein the aryl group is optionally substituted with one or more groups selected from hydroxy, cyano, (C$_{1-6}$)alkyl, (C$_{1-6}$) alkoxy, haloalkoxy, alkylthio, halo, haloalkyl, hydroxyalkyl, nitro, alkoxycarbonyl, amino, alkylamino, alkylsulfonyl, alkylcarbonyl, alkylaminosulfonyl, alkylsulfonylamino, alkylaminocarbonyl, alkylcarbonylamino and phenyl, heterocycyl, wherein the heterocylcyl group is optionally substituted with one or more groups selected from hydroxy, oxo, cyano, (C$_{1-6}$)alkyl, (C$_{1-6}$) alkoxy, haloalkoxy, alkylthio, halo, and haloalkyl, heteroaryl, wherein the heteroaryl is optionally substituted with one or more groups selected from (C$_{1-6}$) alkyl, (C$_{1-6}$)alkoxy, and halogen, or R' and R" together with the nitrogen they are attached may also form a 5- to 7-membered ring, optionally incorporating one additional heteroatom chosen from O, N, or S(O)$_{0-2}$, said ring being optionally substituted with one or two (C$_{1-6}$)alkyl groups;

R$^4$ is (C$_{1-6}$)alkyl, haloalkyl, benzyloxy, diphenylmethyl, —NR$^a$R$^b$, wherein R$^a$ and R$^b$ are as defined herein, —Y-heterocyclyl, —Y-heteroaryl, wherein the heterocyclyl and heteroaryl groups are independently of each other optionally substituted with one or more groups selected from (C$_{1-6}$)alkyl, (C$_{1-6}$)alkoxy, halo, haloalkyl, alkylsulfonyl, alkylaminosulfonyl, and alkylsulfonylamino, and wherein Y is a bond or (C$_{1-3}$)alkylene;

R$^a$ is hydrogen, (C$_{1-6}$)alkyl, haloalkyl, cycloalkyl or aryl, wherein the cycloalkyl or the aryl group are each independently of each other optionally substituted with (C$_{1-6}$)alkyl, (C$_{1-6}$)alkoxy, halo, haloalkyl, and alkylsulfonyl, or R$^a$ and R$^b$ together with the nitrogen they are attached may also form a 5- to 7-membered ring, optionally incorporating one additional heteroatom chosen from O, N, or S(O)$_{0-2}$, said ring being optionally substituted with one or two (C$_{1-6}$)alkyl groups;

R$^b$ is hydrogen or (C$_{1-6}$)alkyl;

R$^5$ is (C$_{1-6}$)alkyl, haloalkyl, —NR$^a$R$^b$, wherein R$^a$ and R$^b$ are as defined above, aryl or heteroaryl, wherein the aryl or heteroaryl are each independently of each other optionally substituted with one or two groups selected from (C$_{1-6}$)alkyl, (C$_{1-6}$)alkoxy, halo, and alkylsulfonyl; and p is an integer from 1 to 2 inclusive;

or prodrugs, individual isomers, racemic or non-racemic mixtures of isomers, and pharmaceutically acceptable salts or solvates thereof.

2. The compound of claim 1, wherein R$^2$ and R$^3$ are —OR', —NO$_2$, —OSO$_2$R', aryl, or hydrogen, with the proviso that R$^2$ and R$^3$ are not both hydrogen.

3. The compound of claim 2, wherein R$^2$ and R$^3$ are hydrogen or —OR', wherein R' is (C$_{1-6}$)alkyl or haloalkyl, with the proviso that R$^2$ and R$^3$ are not both hydrogen.

4. The compound of claim 1, wherein A is —C(O)R$^4$.

5. The compound of claim 4, wherein R$^1$ is (C$_{1-6}$)alkyl.

6. The compound of claim 4, wherein R$^4$ is —NR$^a$R$^b$.

7. The compound of claim 6, wherein R$^a$ is (C$_{1-6}$)alkyl or aryl, and R$^b$ is hydrogen or (C$_{1-6}$)alkyl, or R$^a$ and R$^b$ together with the nitrogen they are attached may also form a 5- to 7-membered ring, optionally incorporating one additional heteroatom chosen from O, N, or S(O)$_{0-2}$, said ring being optionally substituted with one or two (C$_{1-6}$)alkyl groups.

8. The compound of claim 7, wherein R$^a$ and R$^b$ together with the nitrogen they are attached form a piperidine ring, said piperidine ring being optionally substituted with one or two (C$_{1-6}$)alkyl groups.

9. The compound of claim 7, wherein R$^a$ and R$^b$ together with the nitrogen they are attached form a pyrrolidine ring, said pyrrolidine ring being optionally substituted with one or two (C$_{1-6}$)alkyl groups.

10. The compound of claim 7, wherein R$^a$ and R$^b$ together with the nitrogen they are attached form a piperazine ring, said piperazine ring being optionally substituted with one or two (C$_{1-6}$) alkyl groups.

11. The compound of claim 7, wherein R$^a$ and R$^b$ together with the nitrogen they are attached form a morpholine ring, said morpholine ring being optionally substituted with one or two (C$_{1-6}$)alkyl groups.

12. The compound of claim 6, wherein $R^2$ and $R^3$ are hydrogen or —OR', and R' is $(C_{1-6})$alkyl or haloalkyl, with the proviso that $R^2$ and $R^3$ are not both hydrogen.

13. The compound of claim 6, wherein $R^1$ is ethyl or propyl.

14. The compound of claim 4, wherein $R^4$ is $(C_{1-6})$alkyl or haloalkyl.

15. The compound of claim 14, wherein $R^2$ and $R^3$ are hydrogen or —OR', wherein R' is $(C_{1-6})$alkyl or haloalkyl, with the proviso that $R^2$ and $R^3$ are not both hydrogen.

16. The compound of claim 14, wherein $R^1$ is ethyl or propyl.

17. The compound of claim 4, wherein $R^4$ is —Y-heterocyclyl, or —Y-heteroaryl, wherein —Y— is a bond or a $(C_{1-3})$ alkylene.

18. The compound of claim 17, wherein the heteroaryl is selected from the group of furan, thiophene, isoxazole, oxazole, and imidazole.

19. The compound of claim 17, wherein the heterocyclyl is a piperidine group, optionally substituted with one or two $(C_{1-6})$alkyl groups.

20. The compound of claim 17, wherein $R^2$ and $R^3$ are hydrogen or —OR', wherein R' is $(C_{1-6})$alkyl or haloalkyl, with the proviso that $R^2$ and $R^3$ are not both hydrogen.

21. The compound of claim 17, wherein $R^1$ is ethyl or propyl.

22. The compound of claim 1, wherein A is —S(O)$_2$R$^5$.

23. The compound in claim 22, wherein $R^5$ is $(C_{1-6})$alkyl or haloalkyl.

24. The compound of claim 22, wherein $R^5$ is —NR$^a$R$^b$.

25. The compound in claim 24, wherein $R^a$ is $(C_{1-6})$alkyl or aryl, and $R^b$ is hydrogen or $(C_{1-6})$alkyl, or $R^a$ and $R^b$ together with the nitrogen they are attached may also form a 5- to 7-membered ring, optionally incorporating one additional heteroatom chosen from O, N, or S(O)$_{0-2}$, said ring being optionally substituted with one or two $(C_{1-6})$alkyl groups.

26. The compound of claim 25 wherein $R^5$ is aryl.

27. The compound of claim 26 wherein $R^5$ is phenyl, optionally substituted with $(C_{1-6})$alkyl, $(C_{1-6})$alkoxy, halo and alkylsulfonyl.

28. The compound of claim 25, wherein $R^5$ is heteroaryl.

29. The compound of claim 28, wherein the heteroaryl is chosen from the group of furan, thiophene, isoxazole, oxazole, and imidazole, all optionally substituted with one and two $(C_{1-6})$alkyl groups.

30. The compound of claim 1, comprising:
(7-Bromo-1,2,3,4-tetrahydro-naphthalen-2-yl)-(1-methanesulfonyl-piperidin-4ylmethyl)-propyl-amine;
(4-{[(7-Methoxy-1,2,3,4-tetrahydro-naphthalen-2-yl)-propyl-amino]-methyl}-piperidin-1-yl)-piperidin-4-yl-methanone;
(1-Methanesulfonyl-piperidin-4-ylmethyl)-(7-methoxy-1,2,3,4-tetrahydro-naphthalen-2-yl)-propyl-amine;
4-{[(6,7-Dimethoxy-1,2,3,4-tetrahydro-naphthalen-2-yl)-propyl-amino]-methyl}-piperidine-1-carboxylic acid dimethylamide;
(4-{[(7-Methoxy-1,2,3,4-tetrahydro-naphthalen-2-yl)-propyl-amino]-methyl}-piperidin-1-yl)-morpholin-4-yl-methanone;
(1-Methanesulfonyl-piperidin-4-ylmethyl)-(7-methoxy-1,2,3,4-tetrahydro-naphthalen-2-yl)-propyl-amine; and
(4-{[(6,7-Dimethoxy-1,2,3,4-tetrahydro-naphthalen-2-yl)-propyl-amino]-methyl}-piperidin-1-yl)-morpholin-4-yl-methanone.

31. A pharmaceutical composition comprising a therapeutically effective amount of a compound of claim 1 in admixture with an acceptable carrier.

32. The pharmaceutical composition of claim 31, wherein the compound is suitable for administration to a subject having a disease state which is alleviated by treatment with a muscarinic receptor antagonist.

33. A method of treating a subject which comprises administering to the subject with a disease treatable with a muscarinic receptor antagonist a therapeutically effective amount of one or more compounds of claim 1.

34. The method of claim 33, wherein the disease state is associated with smooth muscle disorders comprising diseases of the genitourinary, gastrointestinal tract, orrespiratory states; or cognitive or neurodegenerative disorders.

35. The method of claim 34, wherein the disease state is associated with the genitourinary tract.

36. The method of claim 35, wherein the disease state comprises overactive bladder, detrusor hyperactivity, urgency, frequency, reduced bladder capacity, incontinence episodes, changes in bladder capacity, micturition threshold, unstable bladder contractions, sphincteric spasticity, outlet obstruction, outlet insufficiency, pelvic hypersensitivity, idiopathy conditions, or detursor instability.

37. The method of treatment of claim 34, wherein the disease state comprises respiratory states.

38. The method of treatment of claim 37, wherein the disease state comprises respiratory states from allergies or asthma.

39. The method of treatment of claim 34, wherein the disease state comprises gastrointestinal tract disorders.

40. The method of treatment of claim 34, wherein the disease state comprises cognitive or neurodegenerative disorders.

41. A process for preparing a compound as claimed in claim 1 which process comprises reacting a compound of formula d:

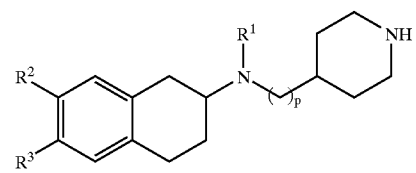

wherein p, $R^1$, $R^2$ and $R^3$ are as described in claim 1, with a compound of formula $R^4C(O)L$ or $R^5S(O)_2L$, wherein L is a leaving group, and $R^4$ and $R^5$ are as described in claim 1, to prepare a compound of Formula I

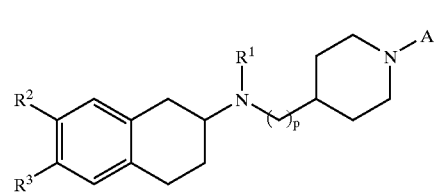

wherein $R^1$, $R^2$, $R^3$, p and A are as described in claim 1.

* * * * *